United States Patent
Hood et al.

(10) Patent No.: US 11,684,291 B2
(45) Date of Patent: Jun. 27, 2023

(54) MONITORING OF PATIENT SUPPORTS

(71) Applicant: Hill-Rom Services, Inc., Batesville, IN (US)

(72) Inventors: Michael S. Hood, Batesville, IN (US); David L. Ribble, Indianapolis, IN (US); Richard H. Heimbrock, Cincinnati, OH (US); Robert M. Zerhusen, Cincinnati, OH (US); Karen Lanning, Batesville, IN (US); Kirsten M. Emmons, Batesville, IN (US); Mary K. Brinkman, Oldenburg, IN (US)

(73) Assignee: Hill-Rom Services, Inc., Batesville, IN (US)

(*) Notice: Subject to any disclaimer, the term of this patent is extended or adjusted under 35 U.S.C. 154(b) by 100 days.

(21) Appl. No.: 17/360,382

(22) Filed: Jun. 28, 2021

(65) Prior Publication Data
US 2021/0321908 A1    Oct. 21, 2021

Related U.S. Application Data

(63) Continuation of application No. 15/092,082, filed on Apr. 6, 2016, now abandoned.
(Continued)

(51) Int. Cl.
*A61B 5/11* (2006.01)
*G16H 40/63* (2018.01)
(Continued)

(52) U.S. Cl.
CPC .......... *A61B 5/1115* (2013.01); *A61B 5/6891* (2013.01); *A61G 7/018* (2013.01);
(Continued)

(58) Field of Classification Search
CPC ..... A61B 5/1115; A61B 5/6891; A61B 5/002; A61B 5/7435; A61B 5/746; A61G 7/018;
(Continued)

(56) References Cited

U.S. PATENT DOCUMENTS 9,138,173 B2   9/2015   Penninger et al.
9,177,465 B2   11/2015  Vanderpohl, III
(Continued)

FOREIGN PATENT DOCUMENTS

EP   3081203 B1   3/2018
EP   3345583 B1   3/2020

OTHER PUBLICATIONS

Search report for related application EP16164926.4 (issued as EP3081203B1), dated Sep. 12, 2016, 9 pages.
(Continued)

*Primary Examiner* — Giovanni Astacio-Oquendo
*Assistant Examiner* — Dilara Sultana
(74) *Attorney, Agent, or Firm* — Barnes & Thornburg LLP

(57) ABSTRACT

A hospital bed is configured to monitor data from a second patient support based on the one or more alarms set by the user. The hospital bed detects whether an alarm triggering event occurred based on the monitored data. In response to a determination that the alarm triggering event occurred, the hospital bed will provide a signal indicative of the alarm triggering event to a nurse call system.

20 Claims, 13 Drawing Sheets

Related U.S. Application Data

(60) Provisional application No. 62/187,450, filed on Jul. 1, 2015, provisional application No. 62/147,239, filed on Apr. 14, 2015.

(51) Int. Cl.

| | | |
|---|---|---|
| *A61G 7/018* | (2006.01) | |
| *A61B 5/00* | (2006.01) | |
| *A61G 7/05* | (2006.01) | |
| *G16H 40/67* | (2018.01) | |
| *G08B 3/10* | (2006.01) | |
| *G08B 5/22* | (2006.01) | |
| *G08B 21/02* | (2006.01) | |
| *G08B 21/04* | (2006.01) | |

(52) U.S. Cl.
CPC .......... *A61G 7/0527* (2016.11); *G08B 3/1016* (2013.01); *G08B 5/226* (2013.01); *G08B 21/0277* (2013.01); *G08B 21/043* (2013.01); *G08B 21/0415* (2013.01); *G08B 21/0461* (2013.01); *G16H 40/63* (2018.01); *G16H 40/67* (2018.01); *A61B 5/002* (2013.01); *A61B 5/746* (2013.01); *A61B 5/7435* (2013.01); *A61G 2203/44* (2013.01)

(58) Field of Classification Search
CPC .............. A61G 7/0527; A61G 2203/44; G08B 3/1016; G08B 5/226; G08B 21/0277; G08B 21/0415; G08B 21/043; G08B 21/0461; G16H 40/63; G16H 40/67
See application file for complete search history.

(56) References Cited

U.S. PATENT DOCUMENTS

| | | | |
|---|---|---|---|
| 9,838,836 B2 | 12/2017 | Hayes et al. | |
| 9,966,997 B2 | 5/2018 | Hayes et al. | |
| 10,290,071 B2 * | 5/2019 | Heil | G16H 20/30 |
| 2008/0016993 A1 | 1/2008 | Campbell et al. | |
| 2008/0021731 A1 | 1/2008 | Rodgers | |
| 2008/0235872 A1 | 10/2008 | Newkirk et al. | |
| 2011/0205061 A1 | 8/2011 | Wilson et al. | |
| 2012/0025992 A1 * | 2/2012 | Tallent | G08B 21/22 |
| | | | 340/573.4 |
| 2013/0076517 A1 | 3/2013 | Penninger et al. | |
| 2014/0080413 A1 * | 3/2014 | Hayes | H04B 5/02 |
| | | | 455/41.1 |
| 2014/0145848 A1 | 5/2014 | Amir | |
| 2014/0184409 A1 | 7/2014 | Vanderpohl, III | |
| 2015/0082542 A1 | 3/2015 | Hayes et al. | |
| 2015/0221198 A1 * | 8/2015 | Collins, Jr. | A61G 7/015 |
| | | | 340/539.17 |
| 2016/0140827 A1 * | 5/2016 | Derenne | A61B 5/6892 |
| | | | 340/573.7 |
| 2016/0235610 A1 | 8/2016 | Drake | |
| 2016/0307429 A1 | 10/2016 | Hood et al. | |

OTHER PUBLICATIONS

Official letter providing grant of related application EP16164926.4 (issued as EP3081203B1), dated Oct. 11, 2017, 44 pages.
Search report for related application EP18157931.9 (issued as EP3345583B1), dated May 24, 2018, 8 pages.
Official letter providing grant of related application EP18157931.9 (issued as EP3345583B1), dated Sep. 18, 2019, 42 pages.

* cited by examiner

MONITORING OF PATIENT SUPPORTS

CROSS-REFERENCE TO RELATED APPLICATIONS

The present application claims priority to U.S. Nonprovisional application Ser. No. 15/092,082, which claims the benefit, under 35 U.S.C. § 119(e), of U.S. Provisional Application Nos. 62/147,239, filed Apr. 14, 2015, and 62/187,450, filed Jul. 1, 2015, each of which is hereby incorporated by reference herein.

BACKGROUND

The present disclosure relates generally to healthcare communication systems such as patient-nurse communication systems, and more particularly to monitoring patient supports usable in connection with such systems.

Healthcare communication systems typically include information and communication technologies to support health services conducted in a healthcare facility setting. For example, some healthcare communication systems include patient-nurse communication systems or "nurse call" systems facilitate communication among members of a nursing staff and other persons dispersed throughout the healthcare facility. The nurse call systems generally provide information about the present status or condition of patients in the healthcare facility, and may additionally provide information regarding status information pertaining to hospital beds throughout the healthcare facility. Visual indicators are often associated with the nurse call systems to visually notify staff of characteristics associated with the hospital beds.

Typically, a member of the nursing staff sets which notifications, or alarms, the nurse call system will provide. For example, the notifications may indicate configurations of the hospital bed, such as whether an upper frame of the hospital bed is in its lowest position relative to a base frame of the hospital bed, whether siderails of the hospital bed are up or down, or whether certain functions of the hospital bed are engaged or disengaged (e.g., whether casters of the hospital bed are braked or unbraked), etc. Further, the notifications may be particular to a patient's condition, such as when a patient of the hospital bed has been identified as a "fall" risk. In other words, it may not be desirable for a fall risk patient to get out of bed unless a caregiver is present in the room to assist the patient. Accordingly, the notifications may include a notification that indicates when a patient exits a hospital bed, for example. Examples of such prior art nurse call systems are Hill-Rom's COMposer™ communication system and Hill-Rom's COMLinx™ communication system.

SUMMARY

The present application discloses one or more of the features recited in the appended claims and/or the following features which, alone or in any combination, may comprise patentable subject matter.

According to a first aspect of the present disclosure, a patient support for use in a healthcare facility having at least one other patient support comprises a display, communication circuitry, and a control system. The display is operable to render a graphical user interface (GUI) to interface with a user. The display is also operable to allow the user to set one or more alarms. Each alarm corresponds to an alarm triggering event triggered by an action of a patient. The communication circuitry is operable to communicatively couple the patient support to a nurse call system and the patient support to the at least one other patient support. The control system is operable to monitor data of the patient support and the at least one other patient support based on the set alarms. The control system detects whether an alarm triggering event has occurred based on the monitored data. In response to a determination that the alarm triggering event occurred, the control system will provide a signal indicative of the alarm triggering event to the nurse call system.

In some embodiments the at least one other patient support comprises at least one of a chair, a toilet, a stretcher, and a lift.

In some embodiments the at least one other patient support comprises a chair, and the alarms include a chair exit alarm to trigger an alarm in response to a determination that a patient previously sitting on the chair is not presently sitting on the chair.

In some embodiments the at least one other patient support comprises a toilet, and the alarms include at least one of an on-toilet alarm to trigger an alarm in response to a determination that a patient has sat on the toilet and an off-toilet alarm to trigger an alarm in response to a determination that a patient previously sitting on the toilet is not presently sitting on the toilet.

In some embodiments the at least one other patient support comprises a stretcher, and the alarms include at least one of a position alarm to trigger an alarm in response to a determination that a present position of the stretcher is in a predetermined position. In some embodiments an exiting alarm may trigger an alarm in response to a determination that the patient is detected as attempting to exit the stretcher. In some embodiments, an out of stretcher alarm may trigger an alarm in response to a determination that the patient has exited the stretcher.

In some embodiments the GUI is further configured to allow the user to control functions of the patient support.

In some embodiments the GUI is further configured to facilitate a wireless network connection between the patient support and the at least one other patient support.

In some embodiments the wireless network connection comprises a Bluetooth network connection.

In some embodiments the GUI is further configured to provide, based on the alarm settings, at least one of a visual indication and an audible noise that the alarm triggering event was detected.

In some embodiments the data comprises a present weight being applied to the patient support and the at least one other patient support.

In some embodiments the event capable of triggering the alarm triggering event includes a position event, an exiting event, and an out of patient support event.

In some embodiments the one or more alarms comprise at least one of one or more alarms of the patient support and one or more alarms of the at least one other patient support.

According to a second aspect of the present disclosure, a system comprises a hospital bed, a patient support communicatively coupled to the hospital bed, and a nurse call system. The hospital bed includes a display operable to render a graphical user interface (GUI) to interface with a user and allow the user to set one or more alarms. Each alarm corresponds to an alarm triggering event. The nurse call system is remote from the hospital bed and the patient support and is communicatively coupled to the hospital bed. The hospital bed is configured to monitor data of the patient support based on the one or more alarms set by the user. The hospital bed will also detect whether an alarm triggering event occurred based on the monitored data. In response to a determination that the alarm triggering event occurred, the hospital bed will provide a signal indicative of the alarm triggering event to the nurse call system.

According to a third aspect of the present disclosure, a patient support for use in a healthcare facility having at least one secondary patient support comprises a display, communication circuitry and a control system. The display is operable to render a graphical user interface (GUI) to interface with a user and allow the user to set one or more alarms. Each alarm corresponds to an alarm triggering event triggered by an action of a patient. The communication circuitry communicatively couples the patient support to a healthcare communication system and the patient support to the at least one secondary patient support. The control system monitors data of the patient support and the at least one secondary patient support based on the set alarms. The control system also detects whether an alarm triggering event occurred at either the patient support or the at least one secondary patient support based on the monitored data. In response to a determination that the alarm triggering event occurred, the control system provides a signal indicative of the alarm triggering event to the healthcare communication system.

In some embodiments, the control system of the patient support determines, from information provided by the secondary patient support, whether a triggering event has occurred at the secondary patient support and provides a signal indicative that the alarm triggering event occurred at the at least one secondary patient support.

In some embodiments, the at least one secondary patient support comprises at least one of a chair, a toilet, a stretcher, and a lift.

In some embodiments, the at least one secondary patient support comprises a chair, and wherein the alarms include a chair exit alarm to trigger an alarm in response to a determination that a patient previously sitting on the chair is not presently sitting on the chair.

In some embodiments, the at least one secondary patient support comprises a toilet, and wherein the alarms include at least one of an on-toilet alarm to trigger an alarm in response to a determination that a patient has sat on the toilet and an off-toilet alarm to trigger an alarm in response to a determination that a patient previously sitting on the toilet is not presently sitting on the toilet.

In some embodiments, In some embodiments, the at least one secondary patient support comprises a stretcher, and wherein the alarms include at least one of a position alarm to trigger an alarm in response to a determination that a present position of the stretcher is in a predetermined position, an exiting alarm to trigger an alarm in response to a determination that the patient is detected as attempting to exit the stretcher, and an out of stretcher alarm to trigger an alarm in response to a determination that the patient has exited the stretcher.

In some embodiments, the GUI is further configured to allow the user to control functions of the patient support.

In some embodiments, the GUI is further configured to facilitate a wireless network connection between the patient support and the at least one secondary patient support.

In some embodiments, the wireless network connection comprises a Bluetooth network connection.

In some embodiments, the GUI is further configured to provide, based on the alarm settings, at least one of a visual indication and an audible noise that the alarm triggering event was detected.

In some embodiments, the data comprises a present weight being applied to the patient support and the at least one secondary patient support.

In some embodiments, the event capable of triggering the alarm triggering event includes a position event, an exiting event, and an out of patient support event.

In some embodiments, the one or more alarms comprise at least one of one or more alarms of the patient support and one or more alarms of the at least one secondary patient support.

In some embodiments, the patient support is a hospital bed.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description refers to the following figures in which.

DETAILED DESCRIPTION

Aspects of the present invention are described with reference to certain illustrative embodiments shown in the accompanying drawings and described herein.

In general, a healthcare communication system includes one or more staff or nursing computers or computing devices, which may be referred to as stations or consoles. The stations or consoles, in cooperation with various computers, networks, and supporting equipment and services, enable nurses and other staff to receive, view, manage, and route, output, or respond to electrical and wireless signals from a variety of communication, call, monitoring, detecting, and/or signaling devices. Some communication, call, monitoring, detecting, and/or signaling devices are activated by patients, staff, or visitors. Others are activated by the occurrence of an event or alarm condition detected by signal receivers, patient monitoring equipment, or patient supports (e.g., hospital beds) located throughout a healthcare facility, such as from sensors integrated into hospital beds. For example, when the healthcare communication system receives a signal from a communication, call, monitoring, detecting, and/or signaling device, one or more indicator assemblies may be activated to alert hospital staff of the condition or event being signaled by the communication, call, monitoring, detecting, and/or signaling device. Accordingly, the hospital staff may respond based on the alarm condition or event signaled by the communication, call, monitoring, detecting, and/or signaling device.

Figure 1:
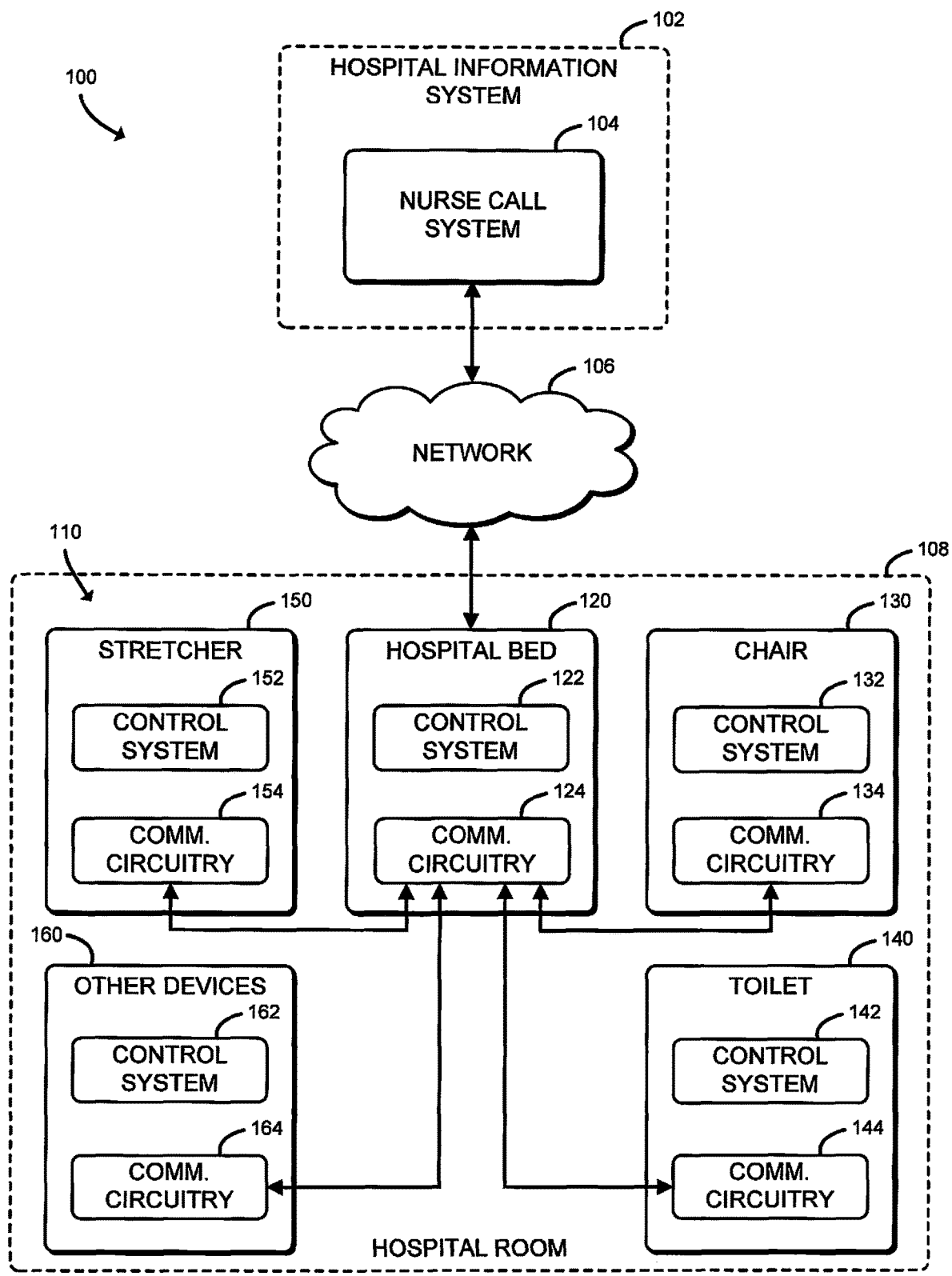
FIG. 1 is a simplified schematic showing a logical architecture for a healthcare communication system that includes a hospital information system in network communication with a hospital bed, and the hospital bed in network communication with one or more additional patient supports.

One such embodiment of a healthcare communication system 100 that may manage communications throughout the healthcare facility is diagrammatically illustrated in FIG. 1. The healthcare communication system 100 includes a hospital information system 102 communicatively coupled via a network 106 to a hospital bed 120. In the illustrative healthcare communication system 100, the hospital information system 102 includes a nurse call system 104. The nurse call system 104 is configured to operate and manage many of the primary nurse call functions of the hospital information system 102. For example, the nurse call system 104 may be configured to receive and manage messages from various connected devices (e.g., the hospital bed 120), coordinate assignment of patients to hospital supports, and/or to synchronize connected devices within the healthcare communication system 100 that are in network communication with the nurse call system 104. Additionally or alternatively, the nurse call system 104 may be configured to answer, control placement of, and cancel calls, as well as, generate notifications or alarms, acknowledge and cancel notifications and alarms, manage location information for staff and devices, activate and deactivate staff, manage staff-patient assignments, assign and manage roles and responsibilities to staff and devices, and/or manage patient information and patient discharges and transfers.

To facilitate the communication requirements of the healthcare communication system 100, the hospital information system 102 may include various computing devices, such as any type of computation or computing device capable of performing the functions described herein, including, without limitation, a server, a blade server, a computer, a desktop computer, a smartphone, a workstation, a laptop computer, a notebook computer, a tablet computer, a mobile computing device, a wearable computing device, a network appliance, a web appliance, a distributed computing system, a processor-based system, and/or a consumer electronic device.

The network 106 may be embodied as any type of wired or wireless communication network, including cellular networks (e.g., Global System for Mobile Communications (GSM), 3G, Long Term Evolution (LTE), Worldwide Interoperability for Microwave Access (WiMAX), etc.), digital subscriber line (DSL) networks, cable networks (e.g., coaxial networks, fiber networks, etc.), telephony networks, local area networks (LANs) or wide area networks (WANs), global networks (e.g., the Internet), or any combination thereof. As previously described, the hospital bed 120 is in communication with the hospital information system 102 via the network 106. Accordingly, the network 106 may include any number of network devices (e.g., access points, routers, switches, servers, etc.) as needed to facilitate communications between the health information system 102 and the hospital bed 120.

The illustrative healthcare communication system 100 additionally includes a chair 130, a toilet 140, and a stretcher 150, collectively referred to herein as other patient supports 110, communicatively coupled to the hospital bed 120. As will be described in further detail below, the hospital bed 120 includes communication circuitry 124 capable of establishing connections and facilitating communications to and from communication circuitry of the chair 130 (i.e., communication circuitry 134), the toilet 140 (i.e., communication circuitry 144), and the stretcher 150 (i.e., communication circuitry 154). Further, as will also be described in further detail below, the hospital bed 120 includes a control system 122 that is capable of controlling operational functionality of the hospital bed. Similarly, each of the chair 130, the toilet 140, and the stretcher 150 include a control system 132, 142, 152 that is capable of controlling operational functionality and/or interpreting data signals from various sensors of the respective other patient supports 110.

While the illustrative healthcare communication system 100 includes a single hospital bed 120 contained within a hospital room 108, it should be appreciated that the healthcare facility may include any number of hospital rooms 108. Accordingly, any number of hospital beds 120 may be located in a healthcare communication system 100 of a healthcare facility and communicatively coupled to the hospital information system 102. It should be further appreciated that the hospital bed 120 may be connected to additional, fewer, or alternative other patient supports 110 (i.e, any number of chairs 130, toilets 140, and stretchers 150). Additionally, it should be appreciated that the types of other patient supports 110 capable of being communicatively coupled to the hospital bed 120 are not limited to the types of patient support of the illustrative healthcare communication system 100, and may include additional or alternative patient supports, such as lifts, slings, and the like.

The illustrative healthcare communication system 100 additionally includes one or more other devices 160. The one or more other devices 160 may include any type of computing device that is capable of being communicatively coupled to the hospital bed 120, such as, without limitation, a computer, a desktop computer, a smartphone, a workstation, a laptop computer, a notebook computer, a tablet computer, a mobile computing device, a wearable computing device, a network appliance, a web appliance, a television, a radio, an audio/visual device, and/or a consumer electronic device. Similar to the other patient supports 110, the other devices 160 each include a control system 162 for controlling the other device 160 and a communication circuitry 164 for establishing and facilitating communication with the hospital bed 120.

Figure 2:
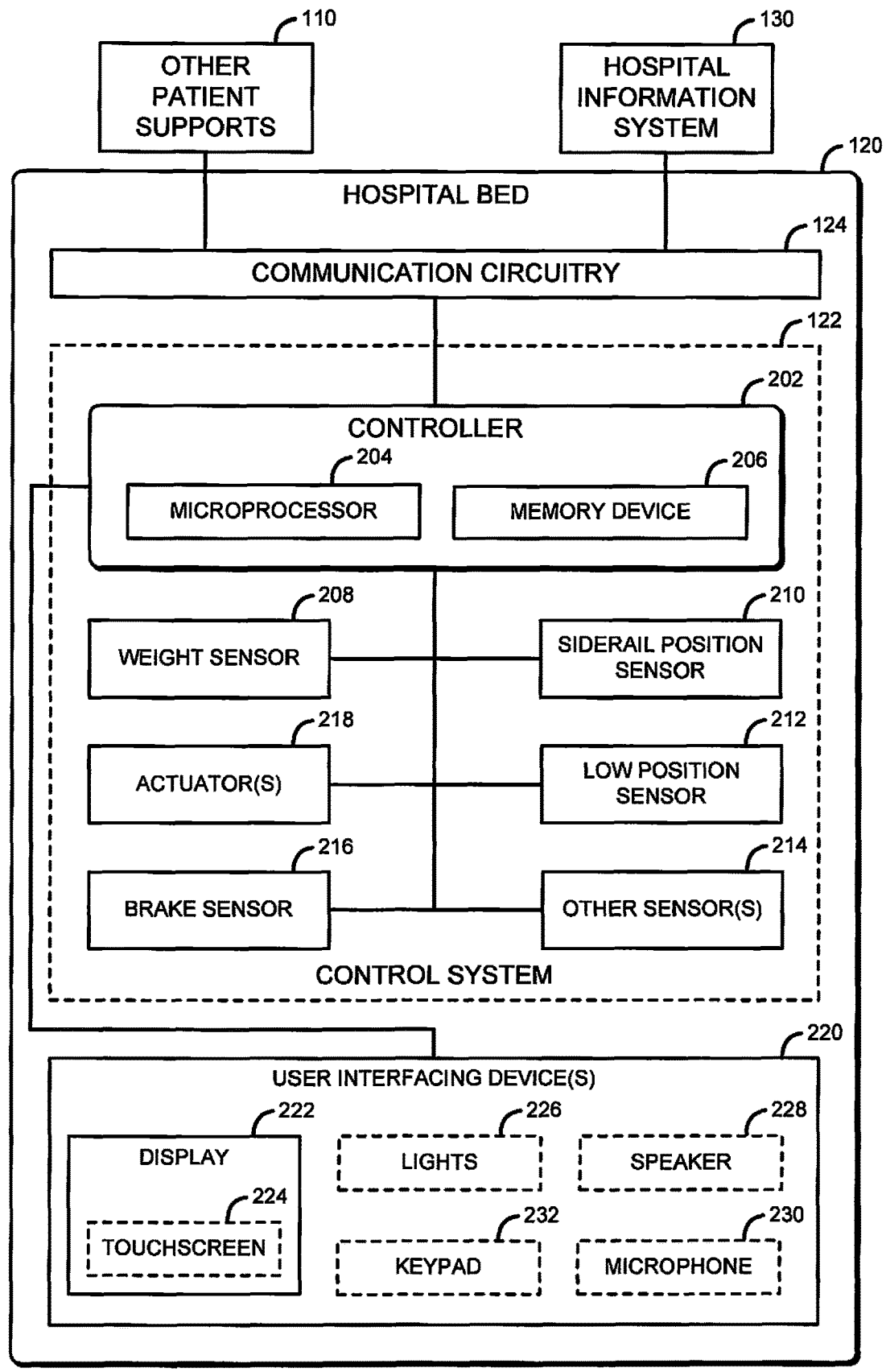
FIG. 2 is a simplified schematic showing physical components of a hospital bed including a number of sensors and showing connectivity to the hospital information system and the additional patient supports of FIG. 1.

As noted previously, each of the hospital bed 120, the other patient supports 110, and the other devices 160 include a control system and communication circuitry. Accordingly, each of the hospital bed 120, the other patient supports 110, and the other devices 160 may have similar electronic components to each other (although perhaps of different computation power, feature capability, and/or robustness). In other words, certain features may not be pervasive between the hospital bed 120, the other patient supports 110, and the other devices 160 such that all the components illustrated in FIG. 2 are representative of the components of other patient supports 110 and the other devices 160. For example, in some embodiments, the hospital bed 120 may be configured to facilitate network communication via wired and wireless technologies using additional or alternative protocols to those supported by the other patient supports 110, which may only support wireless network communication via Bluetooth®, for example. In another example, the hospital bed 120 and the other patient supports 110 may have load cell sensors to detect a weight of a patient; however, the chair 130 and/or the toilet 140 may not have brakes, siderails, and/or adjustable height positions like that of the hospital bed 120, and as such would likely not include sensors and/or actuators typically associated with such features. Those similar components are shown in FIG. 2 and discussed below in regard to the hospital bed 120 with the understanding that such description is equally applicable to the similar components of the other patient supports 110 and the other devices 160 with the understanding that certain differences may exist based on supported features.

FIG. 2 illustrates the physical components of the hospital bed 120, including the control system 122, the communication circuitry 124, and one or more user interfacing devices 220. The control system 122 includes a controller 202 (i.e., an electronic control unit (ECU)), various sensors capable of being monitored and interpreted by the controller 202, and various actuators capable of being controlled by the controller 202. The controller 202 is configured to receive data (i.e., electrical signals) from the various sensors and components of the hospital bed 120, and control the operation of the components of the hospital bed 120 relative to the received data, as is known in the art. To do so, the controller 202 includes a number of electronic components commonly associated with controllers utilized in the control of electromechanical systems. For example, the controller 202 may include, amongst other components customarily included in such devices, a microprocessor 204 and a memory device 206. The memory device 206 may be, for example, a programmable read-only memory device ("PROM") including erasable PROM's (EPROM's or EEPROM's). In use, the memory device 206 is capable of storing, amongst other things, instructions in the form of, for example, a software routine (or routines) which, when executed by the microprocessor 204, allow the controller 202 to control operation of the features of the hospital bed 120.

The illustrative control system 122 additionally includes a weight sensor 208 (e.g., load cells) to sense a weight of a patient assigned to the hospital bed 120, a siderail position sensor 210 to sense whether a siderail of the hospital bed 120 is in raised or lowered positions, a low position sensor 212 to sense whether an upper frame of the hospital bed 120 is in a lowered position relative to a based frame of the hospital bed 120, a brake sensor 214 to sense whether brakes (e.g., casters) of the hospital bed 120 are braked or released, various other sensors 216, and a number of actuators 218 capable of being controlled by the control system to control various components of the hospital bed 120 (e.g., motors, valves, power control units, etc.). The various other sensors may include, but are not limited to, motion sensors, fluid pressure sensors, temperature sensors, level sensors, other position sensors, etc. Each of the sensors 208, 210, 212, 214, 216 and the actuators 218 are electronically coupled to the controller 202.

Similarly, the one or more user interfacing devices 220 are electronically coupled to the controller 202. Accordingly, in some embodiments, the control system 122 may additionally include additional circuitry to convert between analog and digital signals, such as an analog-to-digital (A/D) converter (not shown) or the like. The user interfacing devices 220 may include various input and output devices capable of receiving input from a user (e.g., a patient, hospital staff, caregiver, etc.) and/or providing output to the user related to various sensor and/or configuration data of the hospital bed 120. As described previously, the sensor data may include various sensor readings related to current positions, levels, temperatures, pressure levels, etc. of various components of the hospital bed 120. In some embodiments, the configuration data may include a designated pressure level of component of the hospital bed 120 (e.g., a bladder of a mattress), a designated angle of a headrest portion of the hospital bed 120 relative to a deck of the bed, and/or any other configurable data that may be set by the user and managed by the controller 202.

The illustrative user interfacing devices 220 includes a display 222 that is operable to generate or display a graphical user interface (GUI) to enable the user to interface with components of the hospital bed to control one or more features of the hospital bed 120. As will be described further, the one or more features may include various settings for positioning the components of the hospital bed 120 and setting various alarms and/or notifications based on detected events corresponding to the sensor data. In some embodiments, the display may include a touchscreen 224 capable of generating input data in response to being touched by the user. The touchscreen 224 may be embodied as a resistive touch screen, a capacitive touch screen, a camera-based touch screen, or the like. Further, in some embodiments, the user interface may include a light configuration 226 and/or a speaker 228 to provide status indications of the hospital bed 120 to the user. Accordingly, in such embodiments wherein the user interfacing devices 220 includes an output device, the status indications may be presented at the hospital bed 120. Additionally, in some embodiments, the user interfacing devices 220 may include a keypad 232 (e.g., a keyboard, a touchpad, etc.) for receiving user touch-based inputs and/or a microphone 230 for receiving audible-based inputs. In some embodiments, one or more of the input and/or output devices may be mounted on a siderail of the hospital bed, connected to a control pendant, etc.

The control system 122 is further configured to provide, or relay, the status indications to a remote location, such as the nurse call system 104 of FIG. 1, via the communication circuitry 124. The communication circuitry 124 may be embodied as any communication circuit, device, or collection thereof, capable of enabling communications over the network 106 between the hospital bed 120 and the hospital information system 102, and between the hospital bed 120 and the other patient supports 110. The communication circuitry 124 may be configured to use any one or more communication technologies (e.g., wired or wireless communications) and associated protocols (e.g., Ethernet, Bluetooth®, Zigbee®, Wi-Fi®, WiMAX, etc.) to effect such communication.

As will be described in further detail below, a falls prevention protocol, or falls risk protocol, may be implemented via software being executed on the hospital bed 120. The software is typically comprised of a number of navigable pages, or screens, that a user (e.g., a patient, hospital staff, caregiver, etc.) can interface with to activate alarms associated with the falls prevention protocol. The number of active alarms associated with the falls prevention protocol is based on settings input by the user (i.e., which alarms are activated for a particular hospital bed 120 according to the patient assigned to the hospital bed 120), such as in an alarm settings portion of the software. Upon being armed, an alarm based on the settings may be generated by the hospital bed 120 and transmitted to the nurse call system 104. Such alarms may have a visual component, an audible component, or both. Additionally, other alarms corresponding to one or more of the other patient supports 110 and/or one or more of the other devices 160 communicatively coupled to the hospital bed 120 may be setup via the software being executed on the hospital bed 120. Such workflow software may be, for example, NaviCare® software available from Hill-Rom Company, Inc.

Figure 3:
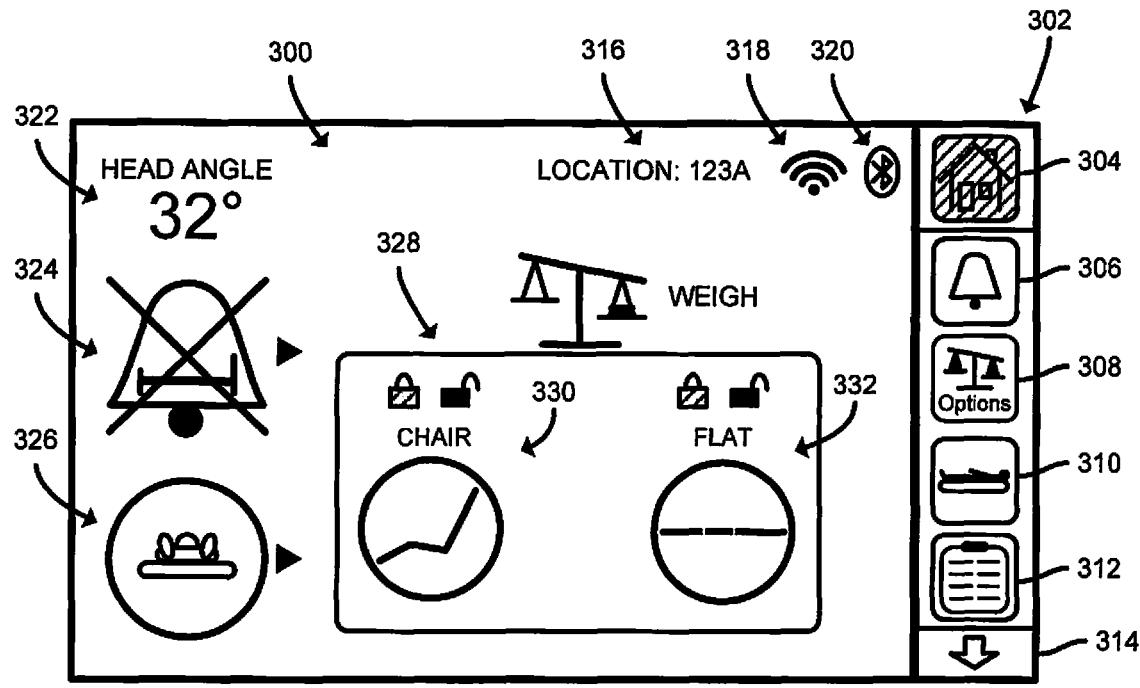
FIG. 3 is a screen shot showing a home screen having a column of main menu icons or buttons on the right hand side of the scale screen and graphical patient weight and hospital bed data associated with the hospital bed of FIG. 1.
Figure 5:
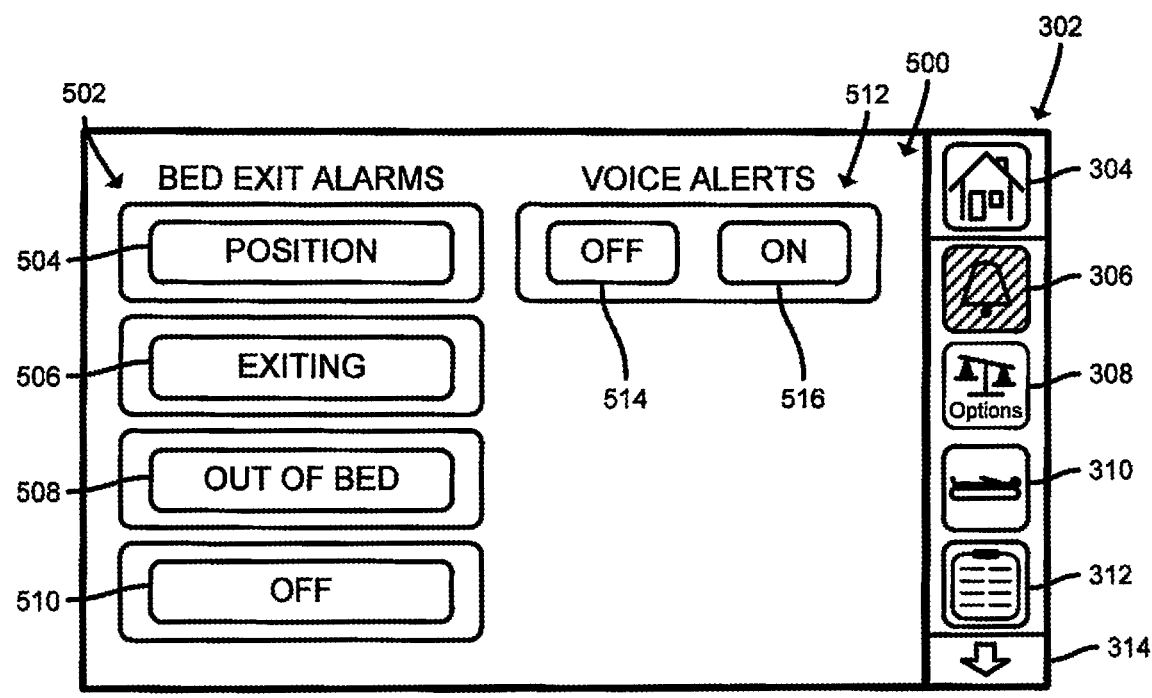
FIG. 5 is a screen shot showing a hospital alarm setting screen having a number of buttons to set or disable various alarms associated with the hospital bed of FIG. 1.

Referring now to FIG. 3, an embodiment of a home screen 300 that is capable of appearing on the display 222 of the hospital bed 120 includes a menu 302 of icons, or virtual buttons, for navigating to other screens. The menu 302 includes a home icon 304, an alarm setup icon 306, a scale setup icon 308, a mattress setup icon 310, and a chart management icon 312. It should be appreciated that not all icons available in the menu 302 may be visible at any given time (i.e., there are too many icons to display in the menu 302). Accordingly, scroll controls, such as a scroll down 314 and a scroll up 604 as shown in FIG. 5, may be displayed on the menu 302 when appropriate. Additionally, the menu 302 may include other icons, such as a Bluetooth pairing icon 602 as shown in FIG. 5. Further, in some embodiments, the menu 302 may additionally or alternatively include other icons, such as icons related to settings of the hospital bed 120, maintenance of the hospital bed 120, etc.

Each menu 302 icon is selectable by the user to navigate between screens, or pages, of the menu 302 corresponding to the menu 302 icons, and each menu 302 option selected provides one or more sub-pages that are related to the navigated to icon. The icons, and associated pages, provide a graphical user interface (GUI) rendered on the display 222 which allow the user to control certain functionality of the hospital bed 120. For example, in some embodiments, selection of the scale setup icon 308 may result in a scale control screen being displayed on the GUI to allow the scale to be setup for the hospital bed 120 and/or one or more other patient supports 110 communicatively coupled to the hospital bed 120. The home icon 304 is the presently active (i.e., toggled "on") icon, as indicated by the cross-hatching on the home icon 304, and accordingly, the home screen 300 is rendered on the GUI of the display 222. It should be appreciated that access to certain screens associated with particular menu 302 icons may be protected such that an identification number, password, and/or biometric associated with the user is required to be entered before access to a restricted screen, or set of screens, is allowed.

The home screen 300 additionally includes a set of bed status indicators, which include a present location indicator 316 (e.g., a hospital room 108 of FIG. 1) of the hospital bed 210 with respect to the facility in which the hospital bed 210 resides, a wireless network strength indicator 318 that indicates a wireless connectivity strength between the to the wireless network (e.g., the network 106 of FIG. 1) and the hospital bed 210, and a Bluetooth enabled state indicator 320 that indicates one or more devices (e.g., the other patient supports 110 of FIG. 1) are presently paired to the hospital bed 210 via Bluetooth. The home screen 300 further includes other bed status indicators, such as a head angle indicator 322 to indicate a present head angle setting of the hospital bed 120, a present alarm state indicator 324 to indicate whether an alarm associated with the hospital bed 120 or the other patient supports 110 is enabled, silenced, or disabled, and a mattress inflation setting indicator 326 to indicate a present inflation level of a mattress of the hospital bed 120. In some embodiments, one or more of the bed status indicators may display additional settings (e.g., enable/disable, adjust level, etc.) related to the indication in response to the user selecting (i.e., clicking on) a particular status indicator enabled to support such interaction.

The home screen 300 includes a weight setup interface 328 that indicates whether the weight for the hospital bed 210 to be used to monitor and trigger alarms has been setup and whether the weight for a patient has been locked in. As shown in the illustrative home screen 300, the weight setup interface 328 includes a chair arrangement indicator 330 and a flat arrangement indicator 332. Each of the chair arrangement indicator 330 and the flat arrangement indicator 332 indicate whether a weight has been setup (i.e., calculated) for each type of arrangement of the hospital bed 210 in which weight can accurately be measured. Additionally, each of the chair arrangement indicator 330 and the flat arrangement indicator 332 include a visual indication as to whether the setup weight presently locked for each arrangement, as indicated by the cross-hatching on the "locked" figures of each of the chair arrangement indicator 330 and the flat arrangement indicator 332.

Figure 4:
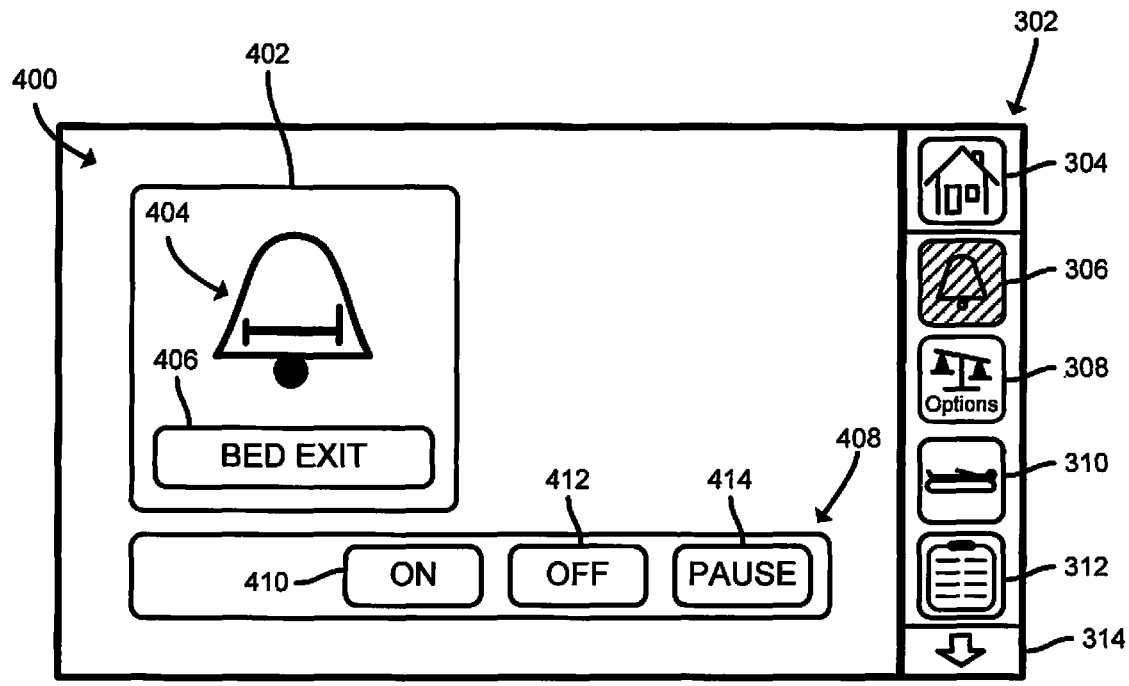
FIG. 4 is a screen shot showing an alarm setup screen having a number of buttons to toggle a state of an alarm associated with the hospital bed of FIG. 1.

Referring now to FIG. 4, an embodiment of an alarm screen 400 that is capable of appearing on the display 222 of the hospital bed 120 includes an alarm notification setup interface 402 and a set of collective alarm setting buttons 408. The alarm screen 400 may appear on the display 222 as a result of the user selecting the alarm setup icon 306 from the menu 302. Accordingly, the alarm setup icon 306 is the presently active (i.e., toggled "on") icon, as indicated by the cross-hatching on the alarm setup icon 306. The alarm notification setup interface 402 includes a visual alarm state indicator 404 that provides a visual indication of the present setting for the hospital bed 120 and a bed exit button 406 that switches the user to a screen that allows the user to view and/or change the state one or more bed exit alarms, an example of which is shown in FIG. 5.

FIG. 5 shows an embodiment of a hospital alarm setting screen 500 that is capable of appearing on the display 222 of the hospital bed 120. The hospital alarm setting screen 500 may appear on the display 222 as a result of the user selecting the bed exit button 406 of FIG. 4. The hospital alarm setting screen 500 may include a number of bed exit alarm buttons 502 that correspond to events that may be trigger an alarm if armed (i.e., on, active, etc.), and voice alerts 512 (i.e., audible noises) associated with the bed exit alarm buttons 502 that have been armed. The events capable of triggering the alarms may be based on a present weight detected by the hospital bed 120, such as when there is no weight on the hospital bed 120 and/or when a weight that corresponds to at least a portion of the patient's weight is detected by the hospital bed 120.

The hospital bed 120 may use any known method(s) by which to detect the present weight, or lack thereof. In some embodiments, load cells may be located in applicable locations of the hospital bed 120 to determine the present weight detected by the hospital bed 120. Accordingly, a weight corresponding to the patient assigned to the hospital bed 120 may be determined and stored in memory (e.g., the memory device 206 of the controller 202 of FIG. 2) of the hospital bed 120 to be used as a baseline to detect alarms associated with the events that correspond to the present weight detected by the hospital bed 120. To do so, the user may have manually entered a weight of the user of used available features of the hospital bed 120 to weigh the patient in one or more arrangements of the hospital bed 120.

The illustrative bed exit alarm buttons 502 include a position alarm button 504 to trigger an alarm when a present position of the hospital bed 120 (e.g., a deck of the hospital bed relative to a base) is in a predetermined position (e.g., its lowest position), an exiting alarm button 506 to trigger an alarm when the user is detected as attempting to exit the hospital bed 120, an out of bed alarm button 508 to trigger an alarm when the user is detected as having exited the hospital bed 120, and an off button 510 to turn off (i.e., disarm) all of the bed exit alarm buttons 502.

As shown, the bed exit alarm buttons 502 may be touched and subsequently toggled to an "on" or "armed" condition, leaving the armed bed exit alarm buttons 502 in a depressed visual state. Additionally or alternatively, in some embodiments, the bed exit alarm buttons 502 may be color coded to indicate their state, such as green for armed and red for disarmed (i.e., off). Accordingly, pressing the off button 510 may release the bed exit alarm buttons 502 from their depressed state, providing a visual indication that the alarms are no longer armed. The voice alerts 512 associated with the bed exit alarm buttons 502 may be toggled off via a voice alert off button 514 or toggled on via a voice alert on button 516.

Referring again to FIG. 4, the collective alarm setting buttons 408 include an on button 410 to turn on all the alarms for the hospital bed 120, an off button 412 to turn off all the alarms for the hospital bed 120, and a pause button 414 to pause all the active alarms for the hospital bed. The collective alarm setting buttons 408 may be user, for example, when a caregiver is performing bedside activities, and such activities may otherwise trigger the alarms associated with the hospital bed 120.

Figure 6:
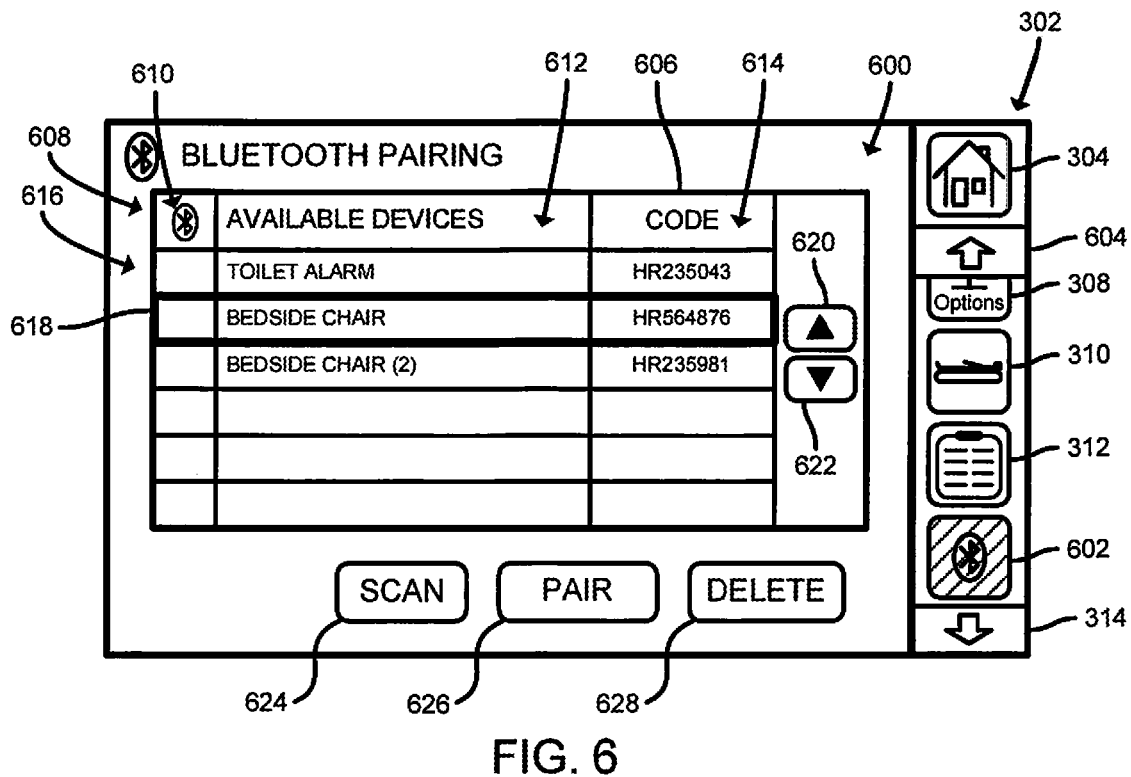
FIG. 6 is a screen shot showing a Bluetooth® pairing screen having a list of Bluetooth compatible devices within range of the hospital bed of FIG. 1.

Referring now to FIG. 6, an embodiment of a Bluetooth pairing screen 600 that is capable of appearing on the display 222 of the hospital bed 120 includes a table 606 that includes a header portion 608 and a body portion 616. The Bluetooth pairing screen 600 may appear on the display 222 as a result of the user selecting the Bluetooth pairing icon 602 from the menu 302. Accordingly, the alarm setup icon 306 is the presently active (i.e., toggled "on") icon, as indicated by the cross-hatching on the alarm setup icon 306. In the illustrative Bluetooth pairing screen 600, the Bluetooth pairing icon 602 is visible in the menu 302 of icons. As a result of the Bluetooth pairing icon 602 not having been visible in the initial state of the illustrative menu 302, the user may have had to select (i.e., press) the scroll down button 314 one or more times to expose the additional icons in the menu 302 until the Bluetooth pairing icon 602 appeared (i.e., was rendered in the menu 302). Accordingly, some of the menu 302 icons that preceded the Bluetooth pairing icon 602 (i.e., the alarm setup icon 306 and the scale setup icon 308) may be completely or at least partially hidden. As a result, the menu 302 additionally displays a scroll up button 604 to allow the user to view the hidden icons of the menu 302.

The body portion 616 includes a list of devices, each on a given row, that are available for pairing with the hospital bed 120 via a Bluetooth connection, such as the other patient supports 110 and the other devices 160 of FIG. 1. The header portion 608 of the table 606 includes a paired status column 610 that displays whether the available device is paired or not with the hospital bed 120, a friendly name column 612 that displays the name of each available device detected by the hospital bed 120 that are Bluetooth capable and have Bluetooth enabled, and a code column 614 that displays a pairing code (i.e., pin code, passcode, passkey, etc.) for each Bluetooth capable device in the list of available devices.

The table 606 additionally includes an up button 620 and a down button 622 for traversing the list of available devices. Accordingly, if the user selects (i.e., presses) the up button 620, an index associated with the selected list item of the list of devices available for pairing is decremented. In turn, a visual indicator of the selected list item may be moved to the list item directly above the previously selected list item. Similarly, if the user selects the down button 622, an index associated with the selected list item of the list of devices available for pairing is incremented. In some embodiments, pressing the up button 620 when the index of the selected list item is equivalent to the first item in the list and pressing the down button 622 when the index of the selected list item is equivalent to the last item in the list, the index may loop to the end or beginning of the list, respectively. As shown in the illustrative Bluetooth pairing screen 600, the presently selected available device 618 is the "bedside chair" (i.e., the chair 130 of FIG. 1) that is the second available device in the list (i.e., the index of the selected list item corresponds to the second item in the list), as indicated by the highlighted rectangle surrounding the available device in the second row of the list in the body portion.

Figure 7:
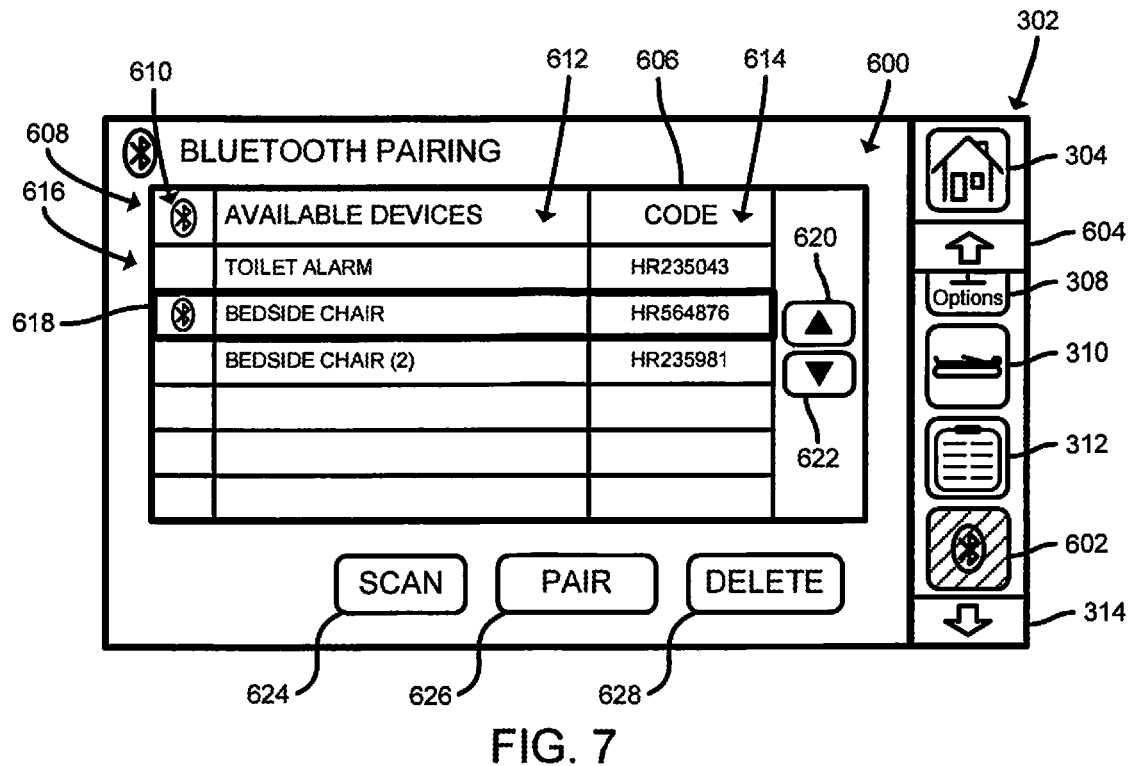
FIG. 7 is a screen shot showing the Bluetooth pairing screen of FIG. 6 having successfully paired to one of Bluetooth compatible devices within range of the hospital bed of FIG. 1.

The Bluetooth pairing screen 600 additionally includes a scan button 624 to re-scan for Bluetooth devices within Bluetooth range of the hospital bed 210 (i.e., re-populate the available device list with Bluetooth devices within the Bluetooth range of the communication circuitry 124 of the hospital bed 210), a pair button 626 to pair the selected available device 618, and a delete button 628 to unpair, or disconnect, the pair between the selected available device 618. Accordingly, in some embodiments, either of the pair button 626 or the delete button 628 may be enabled based on the paired state of the selected available device 618, as indicated by the indication in the paired status column 610 that corresponds to the row of the selected available device 618. As shown, the Bluetooth pairing screen 600 illustrates that the presently selected available device 618 is not paired with the hospital bed 120, as a Bluetooth icon is not presented in the paired status column 610 that corresponds to the row of the presently selected available device 618 (i.e., the second row). Accordingly, the user may select the pair button 626 to initiate the pairing between the hospital bed 120 and the presently selected available device 618. If the pairing is successful, the Bluetooth icon will be displayed in the paired status column 610 that corresponds to the row of the presently selected available device 618, as shown in FIG. 7.

Figure 8:
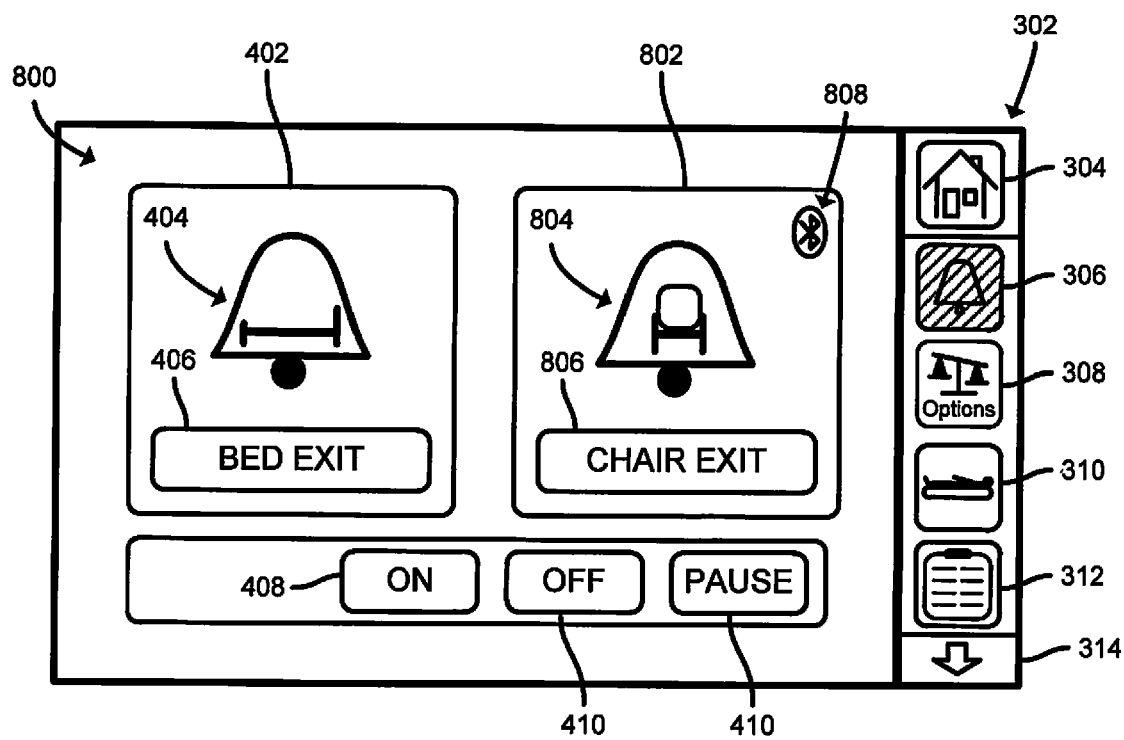
FIG. 8 is a screen shot showing an alarm setup screen having a number of buttons to toggle a state of each alarm associated with the hospital bed of FIG. 1 and each alarm associated with a patient support of FIG. 1 communicatively coupled to the hospital bed.

Referring now to FIG. 8, the alarm screen 400 previously shown in FIG. 4 now includes a chair exit interface 802. The chair exit interface 802 may appear on the alarm screen 400 as a result of a chair 130 having been successfully paired to the hospital bed 120. As described previously, in some embodiments, the chair 130 may include a weight sensor (i.e., a scale) similar to the weight sensor 208 of the illustrative hospital bed 120 of FIG. 2.

In some embodiments, the chair 130 may be configured to transmit weight sensor data to the hospital bed 120 via the Bluetooth connection established between the chair 130 and the hospital bed 120. In such embodiments, the data may be analyzed (e.g., compared against a known weight of a patient as set during setup of the hospital bed 120) to determine whether the patient is sitting on the chair 130. In other words, the hospital bed 120 can determine that the patient is no longer in the hospital bed 120 and detect a weight of an occupant of the chair 130. It should be appreciated that, in some embodiments, the hospital bed 120 may be configured to account for weight offloaded by feet of the occupant being placed on the floor. In other words, a patient sitting in the chair 130 with their feet on the floor may have at least a portion of their weight supported by the floor, and thereby not detected by the weight sensor. To do so, the hospital bed 120 may create and manage a profile for the patient that includes such weight differentials. As such, in some embodiments, the hospital bed 120 may be further configured to automatically set a chair exit alarm for the chair 130 upon detecting the patient sitting in the chair 130.

Figure 9:
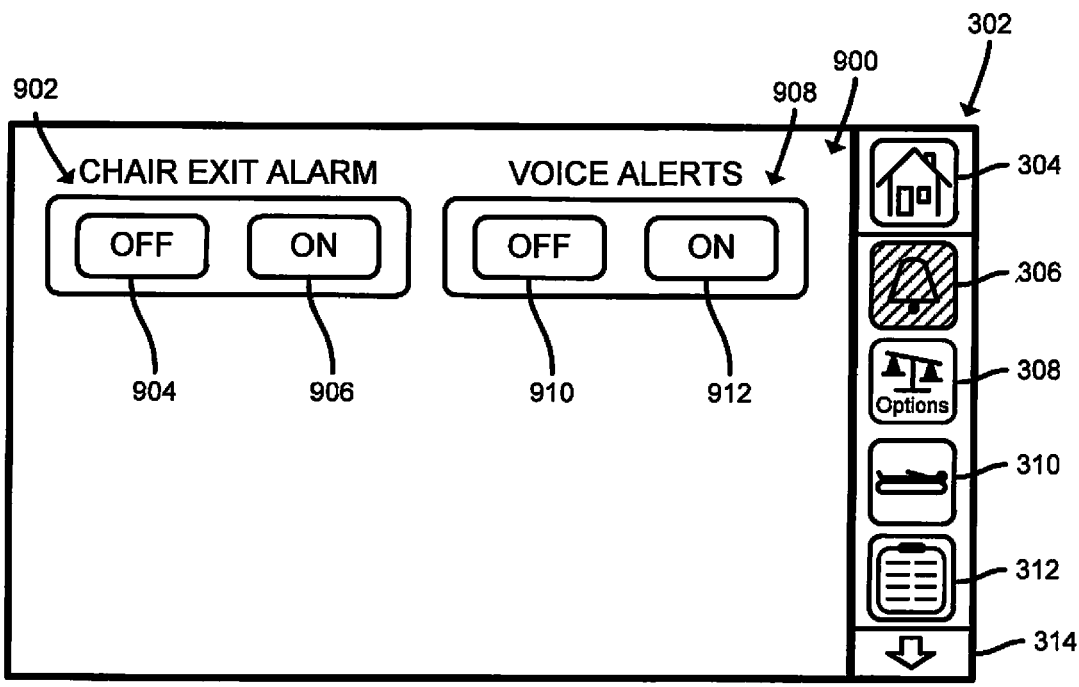
FIG. 9 is a screen shot showing a chair alarm setting screen having a number of buttons to set or disable various alarms associated with a chair in paired communication with the hospital bed of FIG. 1.

The chair exit interface 802 includes a visual alarm state indicator 804 that provides a visual indication of the present setting for the chair 130, a chair exit button 806 that switches the user to a screen that allows the user to view and/or change the state one or more chair exit alarms, an example of which is shown in FIG. 9. Additionally, the chair exit interface 802 includes a visual connection indicator 808 that provides a visual indicate of whether the chair 130 paired to the hospital bed 120 is in present Bluetooth communication with the hospital bed 120. Accordingly, in some embodiments, the visual indicator may be color-coded or visibility toggle, for example, to indicate the state of present Bluetooth communication between the chair 130 and the hospital bed 120.

FIG. 9 shows an embodiment of a chair alarm setting screen 900 that is capable of appearing on the display 222 of the hospital bed 120. The chair alarm setting screen 900 may appear on the display 222 as a result of the user selecting the chair exit button 806 of FIG. 8. The chair alarm setting screen 900 may include a number of chair exit alarms 902 that correspond to events that may trigger an alarm if armed (i.e., on, active, etc.), and voice alerts 512 (i.e., audible noises) associated with the chair exit alarms 902 that have been armed. In the illustrative chair alarm setting screen 900, a single chair exit alarm 902 is provided; however, it should be appreciated that additional and/or alternative chair exit alarms 902 may be provided in other embodiments, such as an exiting alarm similar to that previously described for the hospital bed 120 (i.e., the exiting alarm button 506). It should be appreciated that, in some embodiments, one or more various algorithms (e.g., machine learning algorithms) and/or hysteresis may be used to predict the chair exit prior to the patient completely exiting the chair 130. Accordingly, in such embodiments, the chair exit alarms 902 may include an out of chair alarm similar to the out of bed alarm button 508 to trigger an alarm when the user is detected as attempting to exit the chair 130.

The illustrative chair exit alarm 902 includes an off button 904 to turn off (i.e., disarm) the chair exit alarm and an on button 906 to turn on (i.e., arm) the chair exit alarm. Similar to the bed exit alarm buttons 502 of FIG. 5, the on button 906 and the off button 904 may be touched and subsequently toggled to an "on" or "armed" condition, leaving the selected button in a depressed visual state and the non-selected button in its normal state to provide a visual indication of the state of the chair exit alarm 902. Additionally, similar to the voice alerts 512 associated with the bed exit alarm buttons 502, the chair alarm setting screen 900 includes voice alerts 908 that may be toggled off via a voice alert off button 910 or toggled on via a voice alert on button 912.

Figure 10:
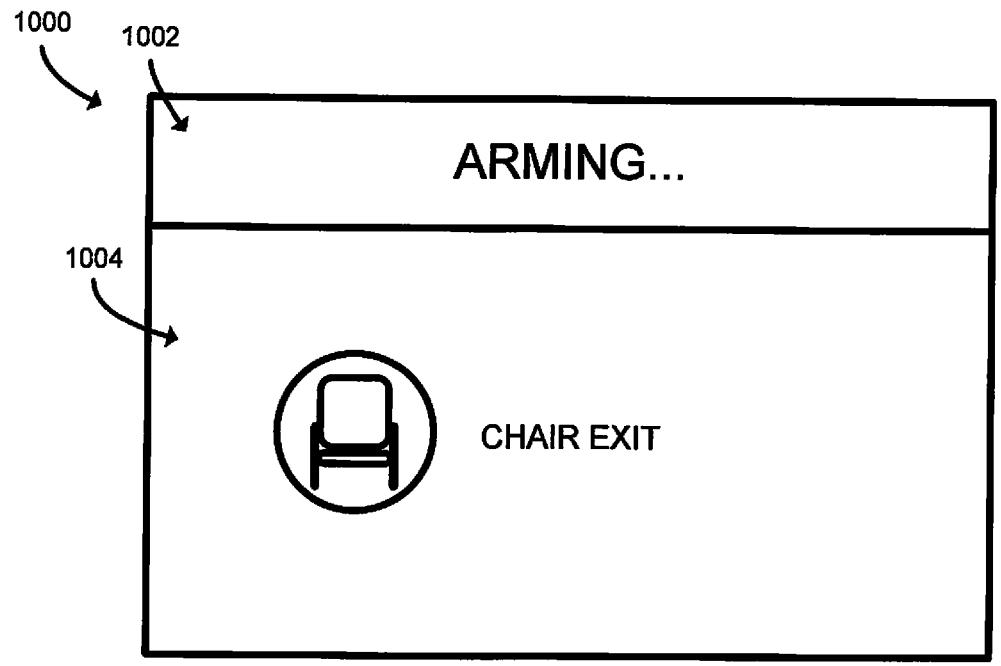
FIG. 10 is a screen shot showing a chair exit arming message dialog having a dialogue header portion that is positioned along the top of the message screen and a dialogue body portion located beneath the dialogue header portion, and indicating that the chair exit alarm is being armed.
Figure 11:
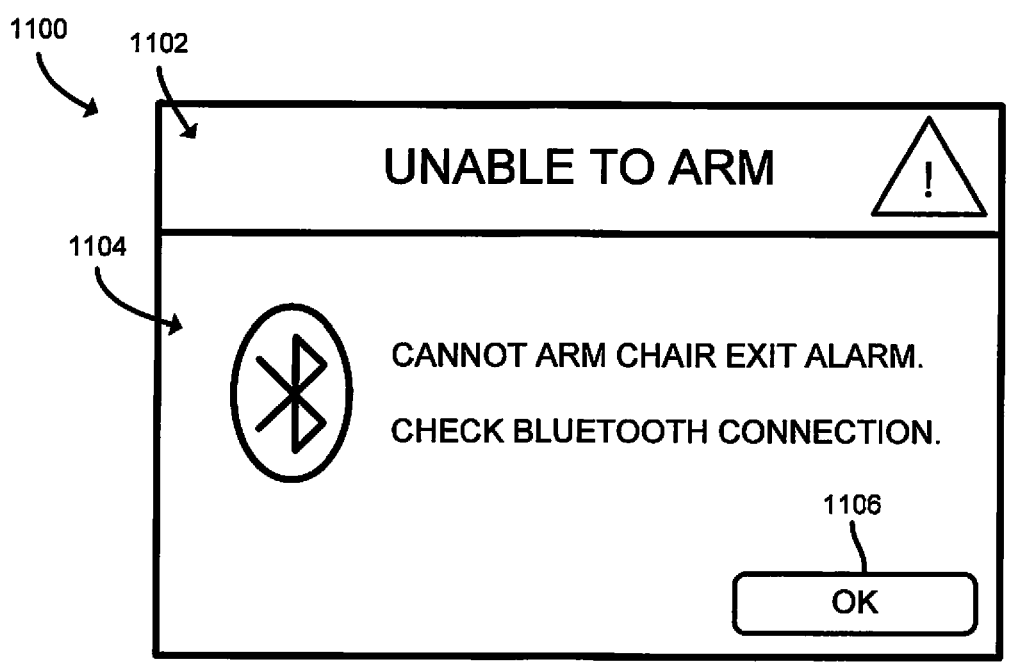
FIG. 11 is a screen shot showing an unable to arm message dialog having a dialogue header portion that indicates an alarm was not able to be armed and a dialogue body portion that provides that the chair exit alarm of FIG. 10 was the alarm that was not able to be armed.
Figure 12:
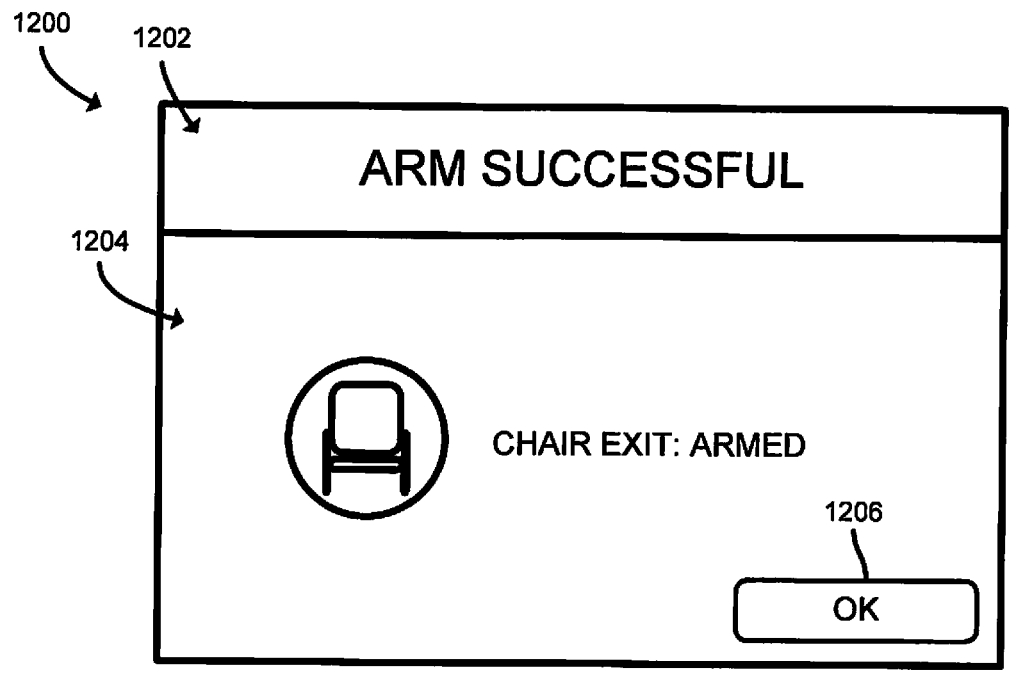
FIG. 12 is a screen shot showing an arm successful message dialog having a dialogue header portion that indicates an alarm was able to be armed and a dialogue body portion that provides that the chair exit alarm of FIG. 10 was the alarm that was armed.

Referring now to FIG. 10, an embodiment of a chair exit arming message dialog 1000 includes a dialogue header portion 1002 that indicates an alert is being armed and a dialogue body portion 1004 that provides that the chair exit is the alert being armed. The chair exit arming message dialog 1000 may appear on the chair alarm setting screen 900 as a result of the user having selected the on button 906 of FIG. 9. If the alert being armed is not successful, a message may be displayed to the user via the display 222 indicating as such. For example, FIG. 11 shows an embodiment of an unable to arm message dialog 1100 that indicates in a dialogue header portion 1102 that an alarm was not able to be armed and further indicates in a dialogue body portion 1104 that the chair exit alarm could not be armed. The unable to arm message dialog 1100 additionally includes a button 1106 to acknowledge the message dialog 1100 and return to the previous screen (e.g., the chair alarm setting screen 900). If the alert being armed is successful, a message may be displayed to the user via the display 222 indicating as such. For example, FIG. 12 shows an embodiment of an arm successful message dialogue 1200 that indicates in a dialogue header portion 1202 that an alarm was able to be armed and further indicates in a dialogue body portion 1204 that the chair exit alarm was successfully armed. The arm successful message dialogue 1200 additionally includes a button 1206 to acknowledge the message dialog 1200 and return to the previous screen (e.g., the chair alarm setting screen 900).

Figure 13:
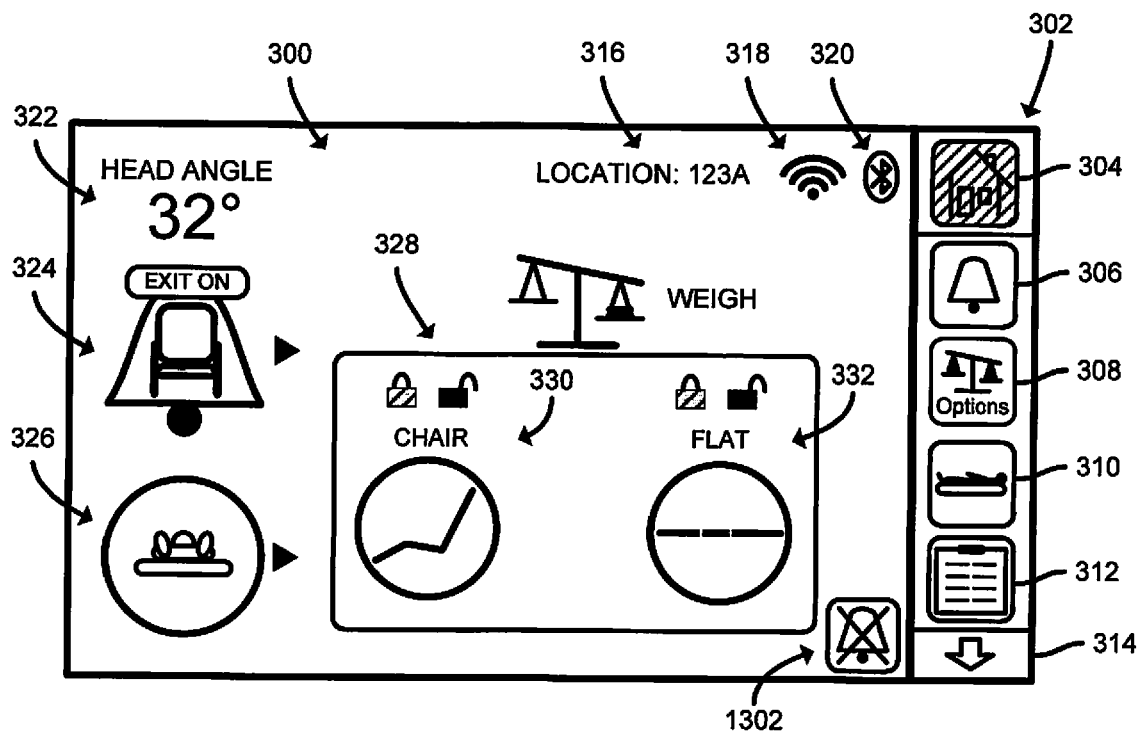
FIG. 13 is a screen shot showing the home screen of FIG. 3 that includes a visual indicator that the chair exit alarm is armed.

In response to one of the other patient supports 110 being paired to the hospital bed 120, one of the other devices 160 being paired to the hospital bed 120, and/or an alert associated with the patient support and/or the other device 160 being armed, various additional indicators may be added to other screens and/or existing indicators may be updated to include additional information. For example, in FIG. 13, the present alarm state indicator 324 of the home screen 300 of FIG. 3 may be updated to include an indication that the chair exit was armed. The home screen 300 may additionally include a silence button 1302 that allows the user to preemptively silence the armed alerts from the home screen 300.

Figure 14:
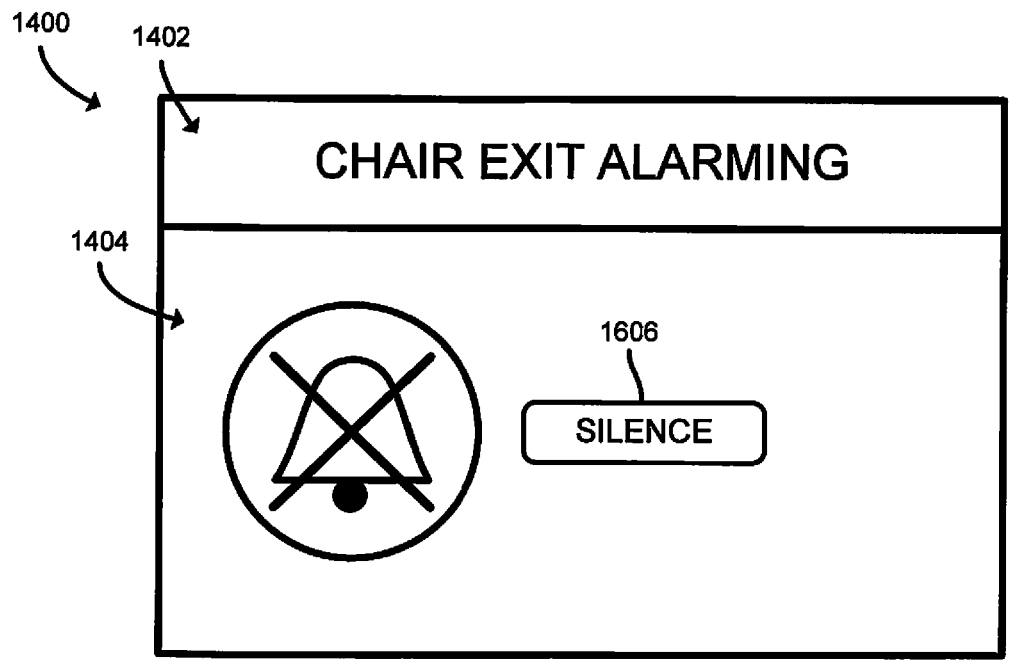
FIG. 14 is a screen shot showing a chair exit alarm message dialogue having a dialogue header portion that indicates the message corresponds to a chair exit alarm and a dialogue body portion that provides a button to silence the chair exit alarm.

Referring now to FIG. 14, an embodiment of a chair exit alarming message dialog 1400 includes a dialogue header portion 1402 that indicates the chair exit alarm has been triggered and a dialogue body portion 1404 that provides a silence button 1406 that silences the alert associated with the chair exit alarm.

Figure 15:
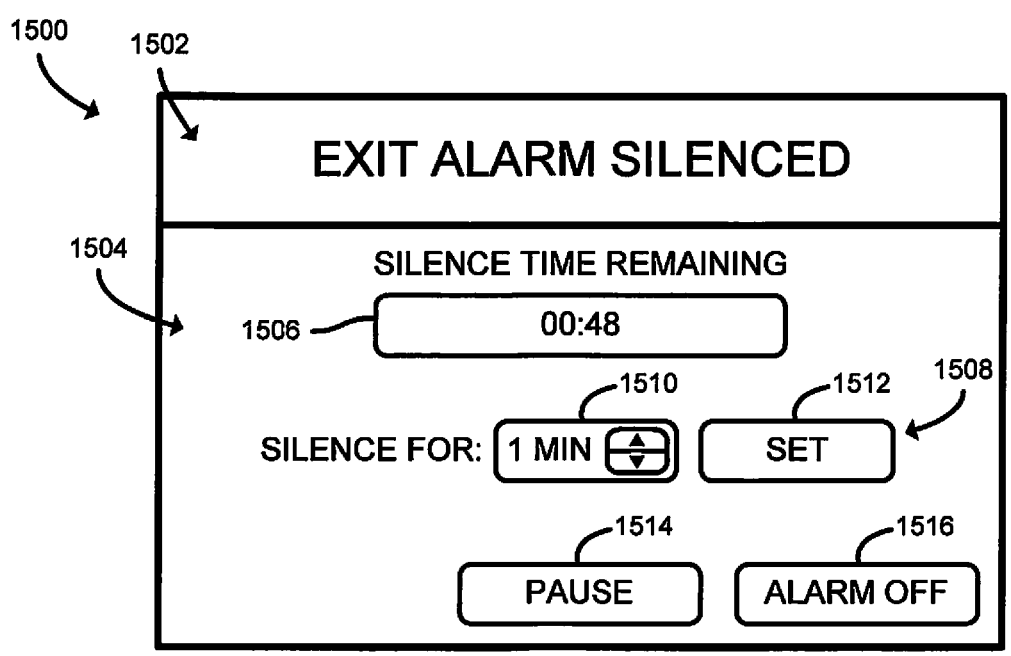
FIG. 15 is a screen shot showing an exiting alarm silenced message dialogue having a dialogue header portion that indicates the message corresponds to a silenced exit alarm and a dialogue body portion that provides various user interface controls to adjust a silence time associated with the exit alarm and turn off the exit alarm.

FIG. 15 shows an embodiment of an exiting alarm silenced message dialogue 1500 that includes a dialogue header portion 1502 that indicates the message corresponds to a silenced exit alarm and a dialogue body portion 1504. The dialogue body portion 1504 includes a time remaining indicator 1506 that provides a countdown that indicates an amount of time remaining until the exit alarm will no longer be silenced. The dialogue body portion 1504 additionally includes a silence duration setting interface 1508 that includes a silence time control 1510 to set a dynamically adjustable amount of time for the silence duration and a set silence time button 1512 to set the silence duration to the amount of time represented by the silence time control 1510. While the illustrative silence time control 1510 includes a spinner control, it should be appreciated that, in alternative embodiments, the silence time control 1510 may be any other type of dynamically adjusted control, such as a drop-down combo-box that includes a predetermined number of time durations from which the user can select. In some embodiments, the silence duration setting interface 1508 may include a single button with a predetermined static time duration that is set when the user selects (i.e., presses) the single button.

Figure 16:
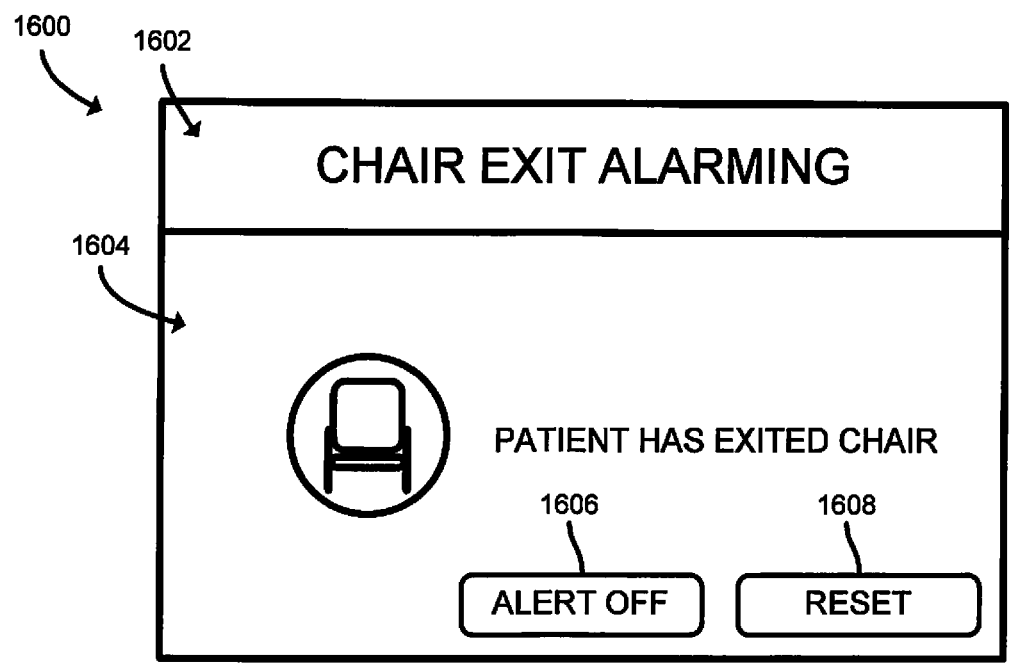
FIG. 16 is a screen shot showing an alternative chair exit alarm message dialogue having a dialogue header portion that indicates the message corresponds to a chair exit alarm and a dialogue body portion that provides an indication that the chair exit alarm has been triggered.

Referring now to FIG. 16, an embodiment of an alternative chair exit alarming message dialog 1600 includes a dialogue header portion 1602 that indicates the chair exit alarm has been triggered and a dialogue body portion 1604 that provides a more verbose textual indication of the alarm and further provides an alert off button 1606 to turn off the alert associated with the chair exit alarm and a reset button 1608 to reset the alert.

Figure 17:
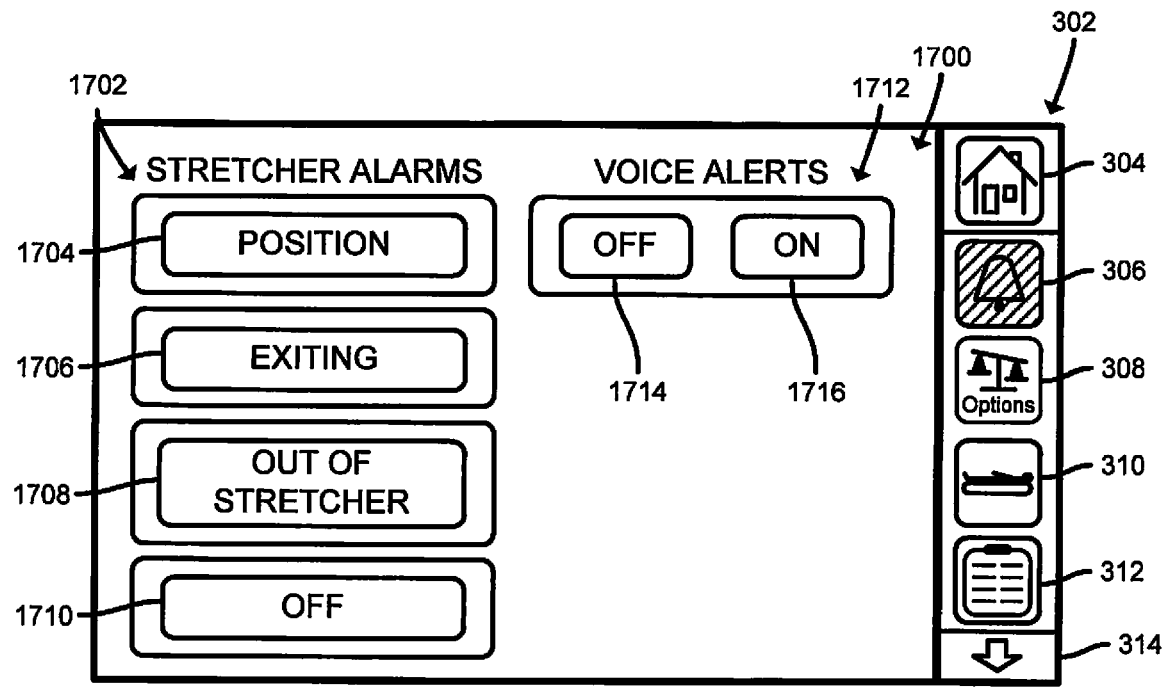
FIG. 17 is a screen shot showing a stretcher alarm setting screen having a number of buttons to set or disable various alarms associated with a stretcher in paired communication with the hospital bed of FIG. 1.
Figure 18:
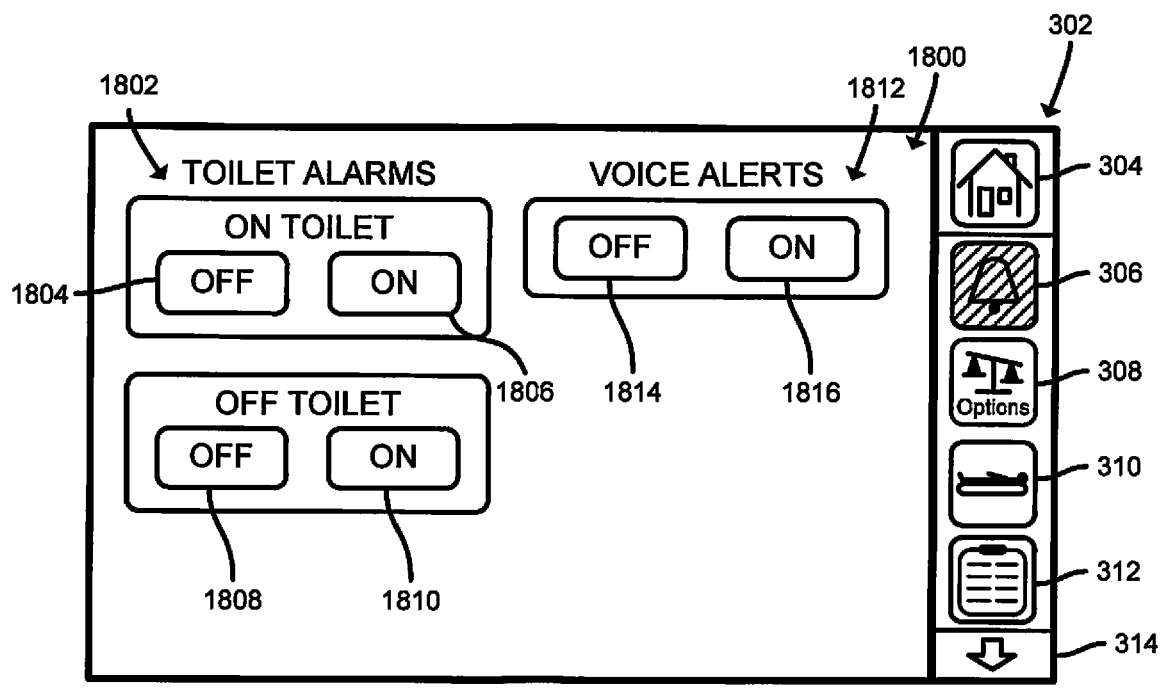
FIG. 18 is a screen shot showing a toilet alarm setting screen having a number of buttons to set or disable various alarms associated with a toilet in paired communication with the hospital bed of FIG. 1.

As described previously, other patient supports 110 other than the chair 130 (e.g., the toilet 140, the stretcher 150, the other devices 160) may be communicatively coupled (e.g., paired via a Bluetooth connection) to the hospital bed 120. FIGS. 17 and 18 illustrate embodiments of the various alarms and alerts associated with the stretcher 150 and the toilet 140, respectively. Referring now to FIG. 17, an embodiment of a stretcher alarm setting screen 1700 that is capable of appearing on the display 222 of the hospital bed 120 is shown. The stretcher alarm setting screen 1700 may appear on the display 222 as a result of the user selecting a stretcher exit button (not shown), similar to the bed exit button 406 of FIG. 4. The stretcher alarm setting screen 1700 may include a number of stretcher exit alarm buttons 1702 that correspond to events that may trigger an alarm if armed (i.e., on, active, etc.), and voice alerts 1712 (i.e., audible noises) associated with the stretcher exit alarm buttons 1702 that have been armed. Similar to the bed exit alarm buttons 502 of FIG. 5, the illustrative stretcher exit alarm buttons 1702 include a position alarm button 1704 to trigger an alarm when a present position of the stretcher 150 is in a predetermined position (e.g., its lowest position), an exiting alarm button 1706 to trigger an alarm when the user is detected as attempting to exit the stretcher 150, an out of stretcher alarm button 1708 to trigger an alarm when the user is detected as having exited the stretcher 150, and an off button 1710 to turn off (i.e., disarm) all of the stretcher exit alarm buttons 1702. The voice alerts 1712 associated with the stretcher exit alarm buttons 1702 may be toggled off via a voice alert off button 1714 or toggled on via a voice alert on button 1716.

Referring now to FIG. 18, an embodiment of a toilet alarm setting screen 1800 that is capable of appearing on the display 222 of the hospital bed 120 is shown. The toilet alarm setting screen 1800 may appear on the display 222 as a result of the user selecting a toilet exit button (not shown), similar to the bed exit button 406 of FIG. 4. The toilet alarm setting screen 1800 may include a number of toilet exit alarms 1802 that correspond to events that may trigger an alarm if armed (i.e., on, active, etc.), and voice alerts 1812 (i.e., audible noises) associated with the toilet exit alarms 1802 that have been armed. The illustrative toilet exit alarm buttons 1802 include an on-toilet off button 1804 and an on-toilet on button 1806 to toggle whether an on-toilet alarm is active (i.e., armed). In other words, the on-toilet alarm toggle buttons 1804, 1806 determine whether the toilet 140 is to monitor for a patient getting on the toilet 140 and provide a signal that indicates to the hospital bed 120 of the patient getting on the toilet 140 upon detection thereof. Additionally, the illustrative toilet exit alarm buttons 1802 include an off-toilet off button 1804 and an off-toilet on button 1806 to toggle whether an off-toilet alarm is active. In other words, the off-toilet alarm toggle buttons 1808, 1810 determine whether the toilet 140 is to monitor for a patient getting off the toilet 140 and provide a signal that indicates to the hospital bed 120 of the patient exiting the toilet 140 upon detection thereof. The voice alerts 1812 associated with the toilet exit alarm buttons 1802 may be toggled off via a voice alert off button 1814 or toggled on via a voice alert on button 1816.

It should be appreciated that, in some embodiments, the GUI screens of the hospital bed 120 described herein may be accessed via a remote computing device, such as a computing device of the nurse call system 104 of FIG. 1.

Figure 19:
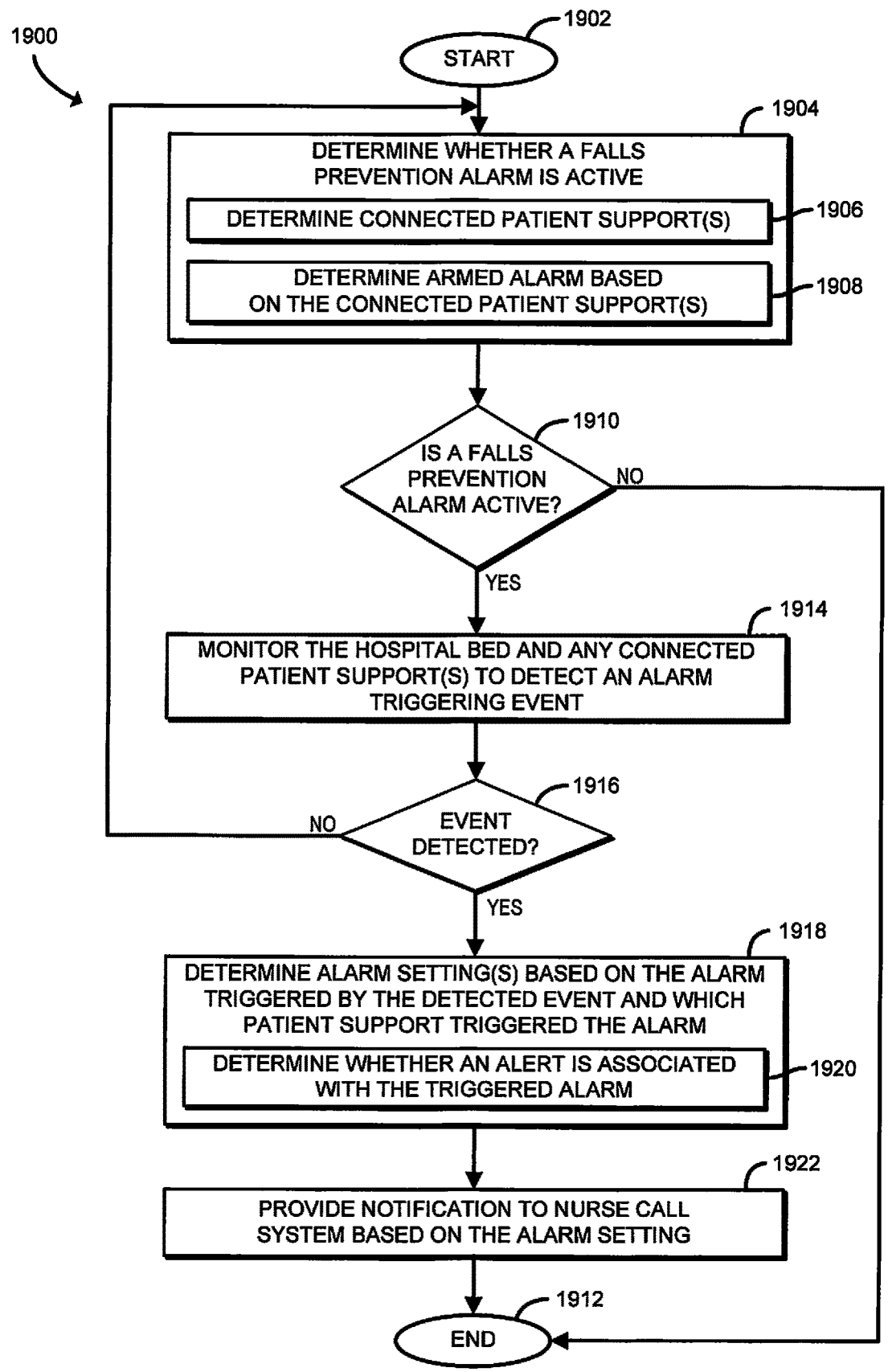
FIG. 19 is a flow diagram of a process for determining whether to provide an alarm signal to a nurse call system of the hospital information system of FIG. 1 that may be executed by the hospital bed of FIG. 1.

Referring now to FIG. 19, a process 1900 for determining whether to provide an alarm signal to the hospital information system 102 of FIG. 1 is shown that may be performed by the hospital bed 120 of FIG. 1. The process 1900 is initialized at step 1902, which may be initiated by a power-on event of the hospital bed 120, for example. The process 1900 proceeds to step 1904, to determine whether a falls prevention alarm is active. As described previously, a falls prevention protocol may be enabled at the hospital bed 120 via one or more alerts associated with the hospital bed 120, the other patient supports 110, and/or the other devices 160.

To do so, the process 1900 proceeds to step 1906 to determine which devices (e.g., the other patient supports 110, the other devices 160, etc.) are connected to the hospital bed 120. From step 1906, the process 1900 proceeds to step 1908 to determine which alarms are armed based on the connected devices determined at step 1906.

The process 1900 then proceeds to step 1910 to determine whether at least one falls prevention alarm is active. In other words, to determine whether an alarm has been armed for at least one of the connected devices determined at step 1906. If no falls prevention alarms are active, the process proceeds to step 1912, wherein the process 1900 terminates. If at least one falls prevention alarm is active, the process 1900 proceeds from step 1910 to step 1914 to monitor the hospital bed 120 and any connected devices with armed (i.e., active) alarms determined at block 1908 to detect whether an alarm triggering event was detected. The process 1900 proceeds from step 1914 to step 1916 to determine whether an alarm triggering event was detected based on monitored data corresponding to the armed alarms associated with the hospital bed 120 and/or the other connected devices determined at step 1906.

If no falls prevention alarms have been triggered, the process 1900 returns to step 1904; otherwise, the process 1900 advances to step 1918 to determine alarm settings based on the triggered falls prevention alarm and which device (e.g., the hospital bed 120 or the other connected devices) triggered the falls prevention alarm. To do so, the process 1900 proceeds to step 1920 to determine whether in alert is associated with the triggered falls prevention alarm for the triggering device. For example, if the chair exit alarm 902 of FIG. 9 has been activated for the chair 130 of FIG. 1 and was subsequently triggered, an alert may also be associated with the chair exit alarm 902, such as the voice alerts 908 of FIG. 9, for example. The process 1900 proceeds to step 1922 to provide a notification to the nurse call system 104 of FIG. 1 based on the alarm setting detected at step 1918. In the previous example of the chair exit alarm, a nurse call signal is sent to the nurse call system 104 in response to the chair exit (i.e., the falls prevention alarm). The nurse call signal may include an indication to trigger a visible alarm (i.e., an alarm dialog displayed on a computing device, an illuminated LED, a text message sent to a mobile computing device, etc.), and may additionally include an indication to produce a voice alert if the voice alerts 908 have been turned on. The process then proceeds from step 1922 to step 1912, wherein the process terminates.

Figure 20:
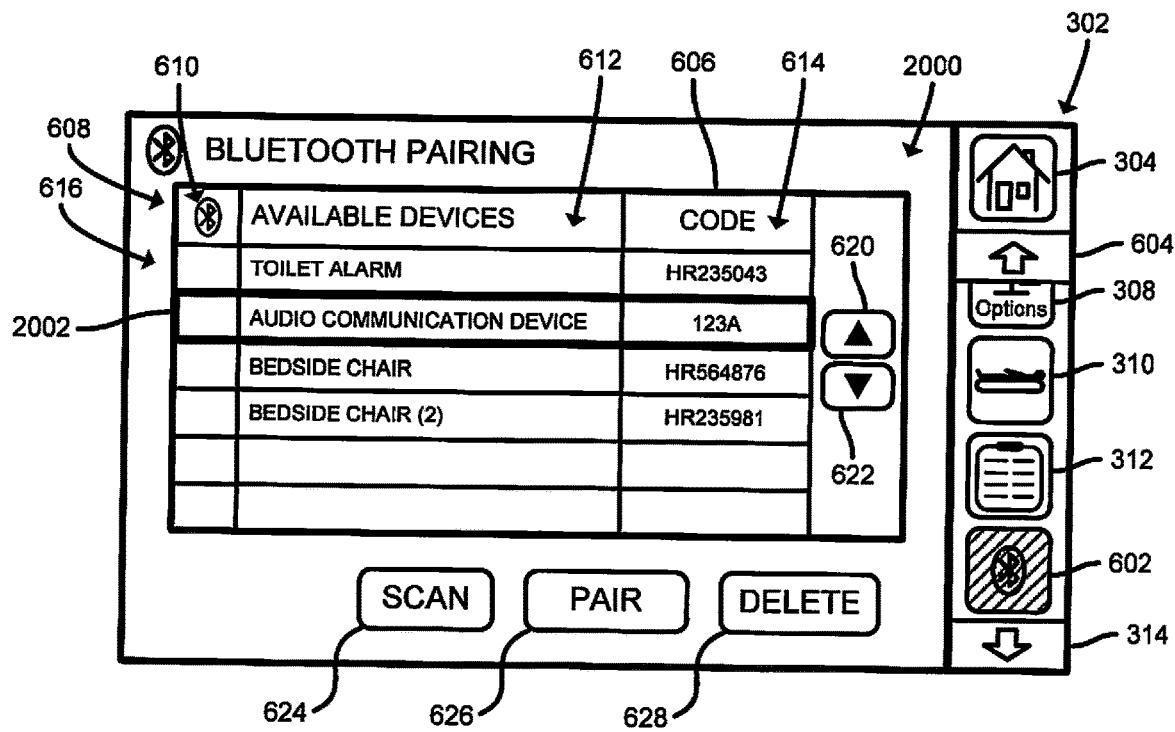
FIG. 20 is a screen shot showing a Bluetooth pairing screen having a list of Bluetooth compatible devices within range of the hospital bed of FIG. 1.

As described previously, the one or more other devices 160 may be wirelessly connected to the hospital bed 120. For example, referring now to FIG. 20, similar to FIG. 6, the body portion 616 includes the list of devices that are available for pairing with the hospital bed 120 via a Bluetooth connection. As shown in the illustrative Bluetooth pairing screen 2000, the presently selected available device 2002 is an "audio communication device" that is indicated as selected by the highlighted rectangle surrounding the available device in the second row of the list of available devices.

Figure 21:
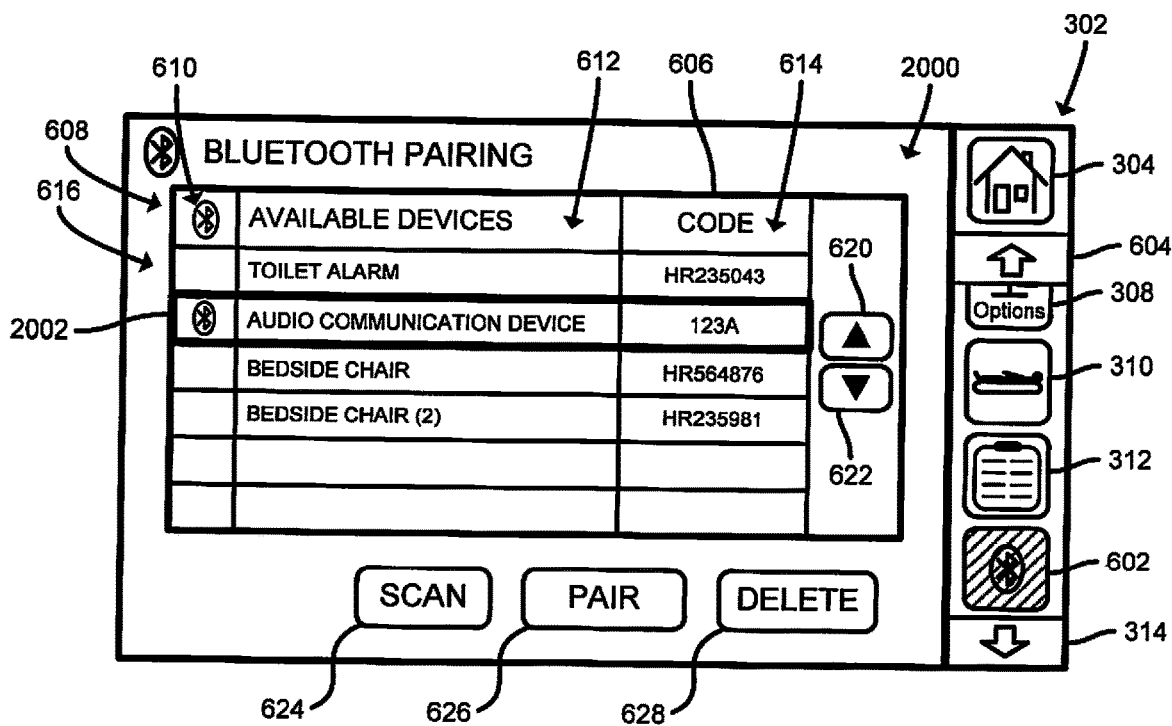
FIG. 21 is a screen shot showing the Bluetooth pairing screen of FIG. 20 having successfully paired to one of Bluetooth compatible devices within range of the hospital bed of FIG. 1.

In an example embodiment, the audio communication device may be an externally located computing device (e.g., a Hill-Rom® SideCom® unit) that is capable of facilitating the reception and transmission of audio communications between the nurse call system 104 and the audio communication device, and/or an audio emitting device (e.g., a radio, a television, etc.) and the audio communication device. Further, the audio communication device is capable of wirelessly transmitting such communications from the audio communication device to a paired device (e.g., the hospital bed 120). As such, upon pairing the audio communication device with the hospital bed 120 (see FIG. 21), the speaker 228 of the hospital bed 120 may emit the communications from the nurse call system 104 and/or the audio emitting device. Similarly, the microphone 230 of the hospital bed 120 may receive communications from the patient and wirelessly transmit the audio communications to the audio emitting device for transmission to the nurse call system 104. It should be appreciated that additional and/or alternative externally compatible Bluetooth connections may also be authorized for pairing with the hospital bed 120 via a wireless connection, such as Bluetooth.

Although certain illustrative embodiments have been described in detail above, variations and modifications exist within the scope and spirit of this disclosure as described and as defined in the following claims. The drawings are provided to facilitate understanding of the disclosure, and may depict a limited number of elements for ease of explanation. Except as may be otherwise noted in this disclosure, no limits on the scope of patentable subject matter are intended to be implied by the drawings.

The invention claimed is:

1. A system for use in a healthcare facility, the system comprising:
   a secondary patient support having a first patient detector operable to detect the presence or absence of a patient on the secondary patient support,
   a bed spaced from the secondary patient support and having a second patient detector operable to detect the presence or absence of a patient on the bed, the bed including a display operable to render a graphical user interface (GUI) to interface with a user and allow the user to set one or more alarms, wherein each alarm corresponds to an alarm triggering event triggered by an action of a patient relative to the bed or secondary patient support;
   communication circuitry on the bed to communicatively couple the bed to a healthcare communication system and to communicatively couple the bed to the secondary patient support; and
   a control system on the bed to monitor data of the bed and the secondary patient support based on the set alarms, detect whether an alarm triggering event occurred at either the bed or the secondary patient support based on the monitored data, and, in response to a determination that the alarm triggering event occurred, provide a signal indicative of the alarm triggering event to the healthcare communication system,
   wherein the GUI is further configured to facilitate a wireless network connection for wireless transfer of alarm data between the bed and the secondary patient support, and
   wherein the GUI of the bed has a user input for setting an alarm of the secondary patient support.

2. The system of claim 1, wherein the control system of the bed determines, from information provided by the secondary patient support, whether a triggering event has occurred at the secondary patient support and provides a signal indicative that the alarm triggering event occurred at the secondary patient support.

3. The system of claim 2, wherein the secondary patient support comprises a chair.

4. The system of claim 3, wherein the alarms include a secondary patient support exit alarm to trigger an alarm in response to a determination that a patient previously supported on the secondary patient support is no longer supported on the secondary patient support.

5. The system of claim 4, wherein the wireless network connection comprises a Bluetooth network connection.

6. The system of claim 5, wherein the GUI is further configured to provide at the GUI, based on the alarm settings, at least one of a visual indication and an audible noise that the alarm triggering event was detected by the secondary patient support.

7. The system of claim 2, wherein the alarms include a secondary patient support exit alarm to trigger an alarm in response to a determination that a patient previously supported on the secondary patient support is no longer supported on the secondary patient support.

8. The system of claim 7, wherein the wireless network connection comprises a Bluetooth network connection.

9. The system of claim 8, wherein the GUI is further configured to provide at the GUI, based on the alarm settings, at least one of a visual indication and an audible noise that the alarm triggering event was detected by the secondary patient support.

10. The system claim 9, wherein the data comprises a present weight being applied to the bed and the secondary patient support.

11. The system of claim 9, wherein the event capable of triggering the alarm triggering event includes a position event, an exiting event, and an out of bed event.

12. The system of claim 9, wherein the one or more alarms comprise at least one of one or more alarms of the bed and one or more alarms of the secondary patient support.

13. The system of claim 1, wherein the secondary patient support comprises a chair.

14. The system of claim 13, wherein the alarms include a secondary patient support exit alarm to trigger an alarm in response to a determination that a patient previously supported on the secondary patient support is no longer supported on the secondary patient support.

15. The system of claim 14, wherein the wireless network connection comprises a Bluetooth network connection.

16. The system of claim 15, wherein the GUI is further configured to provide at the GUI, based on the alarm settings, at least one of a visual indication and an audible noise that the alarm triggering event was detected at the secondary patient support.

17. The system of claim 1, wherein the alarms include a secondary patient support exit alarm to trigger an alarm in response to a determination that a patient previously supported on the secondary patient support is no longer supported on the secondary patient support.

18. The system claim 17, wherein the data comprises a present weight being applied to the bed and the secondary patient support.

19. The system of claim 17, wherein the event capable of triggering the alarm triggering event includes a position event, an exiting event, and an out of bed event.

20. The system of claim 17, wherein the one or more alarms comprise at least one of one or more alarms of the bed and one or more alarms of the secondary patient support.

* * * * *

UNITED STATES PATENT AND TRADEMARK OFFICE
CERTIFICATE OF CORRECTION

PATENT NO. : 11,684,291 B2
APPLICATION NO. : 17/360382
DATED : June 27, 2023
INVENTOR(S) : Michael S. Hood et al.

Page 1 of 1

It is certified that error appears in the above-identified patent and that said Letters Patent is hereby corrected as shown below:

In the Claims

Column 19, Line 22, Claim 10, after the word "system" insert the word --of--.

Column 20, Line 20, Claim 18, after the word "system" insert the word --of--.

Signed and Sealed this
Fifteenth Day of August, 2023

Katherine Kelly Vidal
*Director of the United States Patent and Trademark Office*